(12) United States Patent
Watanabe

(10) Patent No.: US 11,421,252 B2
(45) Date of Patent: Aug. 23, 2022

(54) METHOD FOR PRODUCING 3,5-DIHYDROXY-4-METHOXYBENZYL ALCOHOL FROM PLANKTON

(71) Applicant: Watanabe Oyster Laboratory Co., Ltd., Tokyo (JP)

(72) Inventor: Mitsugu Watanabe, Tokyo (JP)

(73) Assignee: WATANABE OYSTER LABORATORY CO., LTD., Tokyo (JP)

( * ) Notice: Subject to any disclaimer, the term of this patent is extended or adjusted under 35 U.S.C. 154(b) by 36 days.

(21) Appl. No.: 17/265,974

(22) PCT Filed: Jul. 25, 2019

(86) PCT No.: PCT/JP2019/029201
§ 371 (c)(1),
(2) Date: Feb. 4, 2021

(87) PCT Pub. No.: WO2020/031720
PCT Pub. Date: Feb. 13, 2020

(65) Prior Publication Data
US 2021/0310030 A1    Oct. 7, 2021

(30) Foreign Application Priority Data

Aug. 7, 2018 (JP) ............................. JP2018-148628
Mar. 20, 2019 (JP) ............................. JP2019-053147

(51) Int. Cl.
*C12N 1/12*   (2006.01)
*C12P 7/22*   (2006.01)

(52) U.S. Cl.
CPC ................................ *C12P 7/22* (2013.01)

(58) Field of Classification Search
CPC ...................................... C12N 1/12; C12P 7/22
See application file for complete search history.

(56) References Cited

FOREIGN PATENT DOCUMENTS

| JP | 2016-42825 | 4/2016 | | |
|----|------------|--------|---|---|
| JP | 2017-132753 | 8/2017 | | |
| JP | 2018-118910 | 8/2018 | | |
| JP | 2019-029201 | * | 7/2019 | ............... C12N 1/12 |

OTHER PUBLICATIONS

International Search Report (ISR) dated Oct. 8, 2019 in International (PCT) Application No. PCT/JP2019/029201.
Mitsugu Watanabe et al., "A phenolic antioxidant from the Pacific oyster (*Crassostrea gigas*) inhibits oxidation of cultured human hepatocytes mediated by diphenyl-1-pyrenylphosphine", Food Chemistry, vol. 134, pp. 2086-2089, ISSN: 0308-8146, 2012.
Mitsugu Watanabe et al., "Isolation and Characterization of a Phenolic Antioxidant from the Pacific Oyster (*Crassostrea gigas*)", Journal of Agricultural and Food Chemistry, vol. 60, No. 3, pp. 830-835, ISSN: 0021-8561, 2012.

* cited by examiner

*Primary Examiner* — Tekchand Saidha
(74) *Attorney, Agent, or Firm* — Wenderoth, Lind & Ponack, L.L.P.

(57) ABSTRACT

[Problem] The purpose of the present invention is to provide a method for collecting seawater that contains plankton and generating DHMBA (dba), which is an antioxidant, from the plankton contained in the seawater. [Solution] The present invention is characterized in that: collected seawater containing plankton is filtered using a filter, the cell contents are removed from the plankton remaining on the filter, the removed cell contents are subsequently heated, and 3,5-dihydroxy-4-methoxybenzyl alcohol is produced from the heated product; and the plankton are assumed to be diatoms.

14 Claims, 29 Drawing Sheets

H7-09-18S
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Fistulifera soleris gene for 18S ribosomal RNA, partial sequence | 1027 | 1027 | 100.00% | 0 | 93.88% | AB769357.1 | Diatom |
| 2 | 2 | Pedospumella encystans voucher B 40 00408?1 18S ribosomal RNA gene, partial sequence | 843 | 843 | 100.00% | 0 | 89.00% | AY651083.1 | Golden algae |
| 3 | 3 | Heterococcus fuornensis partial 18S rRNA gene, strain SAG 835-5 | 832 | 832 | 100.00% | 0 | 88.71% | AM490826.1 | Yellow-green algae |
| 4 | 4 | Heterococcus caespitosus partial 18S rRNA gene, strain SAG 835-2a | 832 | 832 | 100.00% | 0 | 88.71% | AM490820.1 | Yellow-green algae |
| 5 | 5 | Chlorellidium tetrabotrys partial SAG811-1 18S ribosomal RNA gene, partial sequence | 821 | 821 | 100.00% | 0 | 88.45% | FJ038692.1 | Yellow-green algae |
| 6 | 5 | Spumella vulgaris isolate 1999m 18S ribosomal RNA gene, partial sequence | 821 | 821 | 100.00% | 0 | 88.47% | DQ388532.1 | Golden algae |
| 7 | 7 | Sphaerosorus composita partial 18S rRNA gene, strain SAG 53.91 | 809 | 809 | 100.00% | 0 | 88.12% | AJ579333.1 | |
| 8 | 8 | Bumilleriopsis pyrenoidosa partial 18S rRNA gene, strain SAG 69.80 | 802 | 802 | 100.00% | 0 | 87.99% | AJ579332.1 | |
| 9 | 9 | Pseudotetraedriella kamillae strain SAG 2056 18S ribosomal RNA gene, partial sequence | 778 | 778 | 100.00% | 0 | 87.39% | EF044311.1 | |
| 10 | 9 | Heterococcus brevicellus strain SAG 18.99 culture collection SAG:18.99 18S ribosomal RNA gene, partial sequence | 778 | 778 | 100.00% | 0 | 87.41% | AF251496.1 | |
| 11 | 11 | Monodus unipapilla partial 18S rRNA gene, strain SAG 8.83 | 767 | 767 | 100.00% | 0 | 87.11% | AM490827.1 | |
| 12 | 12 | Vischeria helvetica strain isolate SAG 876-1 18S rRNA gene, complete sequence | 763 | 763 | 100.00% | 0 | 86.98% | JX183080.1 | |
| 13 | 13 | Eustigmatos polyphem strain SAG 38.84 18S ribosomal RNA gene, complete sequence | 758 | 758 | 100.00% | 0 | 86.84% | JX274590.1 | |
| 14 | 13 | Eustigmatos polyphem strain SAG 38.84 18S ribosomal RNA gene, complete sequence | 758 | 758 | 100.00% | 0 | 86.84% | JX183077.1 | |
| 15 | 15 | Ochromonas danica strain SAG933.7 18S rRNA gene, partial sequence | 749 | 749 | 96.00% | 0 | 90.02% | JQ281814 | |
| 16 | 16 | Monodus unipapilla culture SAG:8.83 voucher SAG 8.83 18S ribosomal RNA (ssu) gene, partial sequence | 728 | 728 | 100.00% | 0 | 86.89% | HQ710565.1 | |
| 17 | 17 | Sargassococcus simulans strain CCMP1996 18S ribosomal RNA gene, partial sequence | 719 | 719 | 100.00% | 0 | 85.88% | MF927481.1 | |
| 18 | 17 | Pelagococcus subviridis strain CCMP1410 18S ribosomal RNA gene, partial sequence | 719 | 719 | 100.00% | 0 | 85.90% | MF927480.1 | |
| 19 | 19 | Sargassococcus epiphyticus strain CCMP1995 18S ribosomal RNA gene, partial sequence | 708 | 708 | 100.00% | 0 | 85.53% | MF927478.1 | |
| 20 | 20 | Lagenidium sp. PWL-2010: strain CBS 127042 18S small subunit ribosomal RNA gene, partial sequence | 686 | 686 | 100.00% | 0 | 85.65% | GU073468.1 | |
| 21 | 21 | Geranomyces variabilis voucher MP03 18S rRNA gene, partial sequence: from TYPE material | 682 | 682 | 100.00% | 0 | 84.65% | NG_061114.1 | |
| 22 | 21 | Thoreauomyces humboldti JEL 95 18S rRNA gene, partial sequence: from TYPE material | 682 | 682 | 100.00% | 0 | 84.63% | NG_061113.1 | |
| 23 | 21 | Geranomyces kaneisis voucher JEL569 18S small subunit ribosomal RNA gene, partial sequence | 682 | 682 | 100.00% | 0 | 84.65% | HQ901746.1 | |
| 24 | 24 | Spumella rivalis strain AR4A6 18S ribosomal RNA gene, partial sequence | 671 | 671 | 100.00% | 0 | 85.65% | GU073468.1 | |
| 25 | 24 | Finicolochytrium jerseii JEL 538 18S rRNA gene, partial sequence: from TYPE material | 671 | 671 | 100.00% | 0 | 84.63% | NG_061114.1 | |
| 26 | 24 | Thoreauomyces humboldti JEL 95 18S rRNA gene, partial sequence: from TYPE material | 671 | 671 | 100.00% | 0 | 84.63% | NG_061113.1 | |
| 27 | 24 | Geranomyces kaneisis voucher JEL569 18S small subunit ribosomal RNA gene, partial sequence | 671 | 671 | 100.00% | 0 | 84.65% | HQ901746.1 | |
| 28 | 28 | Thoreauomyces humboldti voucher JEL95 18S small subunit ribosomal RNA gene, partial sequence: from TYPE material | 665 | 665 | 100.00% | 0 | 84.63% | HQ901727.1 | |
| 29 | 28 | Finicolochytrium alabamae voucher JEL 538 18S rRNA gene, partial sequence: from TYPE material | 665 | 665 | 100.00% | 0 | 84.51% | NG_062391.1 | |
| 30 | 28 | Finicolochytrium alabamae voucher JEL538 16S small subunit ribosomal RNA gene, partial sequence | 665 | 665 | 100.00% | 0 | 84.51% | HQ901734.1 | |
| 31 | 29 | Myxozyma neglecta 18S rRNA gene, partial sequence: from TYPE material | 645 | 645 | 99.00% | 0 | 84.03% | NG_062046.1 | |
| 32 | 29 | Myxozyma neglecta strain NRRL Y-27508 18S ribosomal RNA gene, partial sequence | 645 | 645 | 99.00% | 0 | 84.03% | DQ519022.1 | |
| 33 | 29 | Myxozyma mucilagena strain NRRL Y-11833 18S ribosomal RNA gene, partial sequence | 645 | 645 | 99.00% | 0 | 84.03% | DQ519021.1 | |

Fig.11

H7-08-28S_D2R2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Chlorellidium tetrabotrys strain SAG611-1 28S ribosomal RNA gene, partial sequence | 233 | 233 | 48.00% | 2.00E-58 | 84.94% | FJ030861.1 | Yellow-green algae |
| 2 | 2 | Fimicolochytrium jonesii JEL 569 28S rRNA gene, partial sequence; from TYPE material | 224 | 224 | 48.00% | 1.00E-55 | 84.26% | NG_060391.1 | Fungus |
| 3 | 2 | Fimicolochytrium jonesii voucher JEL569 28S large subunit ribosomal RNA gene, partial sequence | 224 | 224 | 48.00% | 1.00E-55 | 84.26% | HQ901681.1 | Fungus |
| 4 | 4 | Geranomyces variabilis voucher MP03 28S large subunit ribosomal RNA gene, partial sequence | 219 | 219 | 48.00% | 5.00E-54 | 84.03% | HQ901692.1 | Fungus |
| 5 | 5 | Thoreauomyces humboldti JEL 95 28S rRNA gene, partial sequence; from TYPE material | 217 | 217 | 48.00% | 2.00E-53 | 83.96% | NG_059928.1 | Fungus |
| 6 | 5 | Thoreauomyces humboldti JEL 95 28S large subunit ribosomal RNA gene, partial sequence | 217 | 217 | 48.00% | 2.00E-53 | 83.96% | HQ901662.1 | Fungus |
| 7 | 5 | Spizellomyces acuminatus 28S ribosomal RNA (LSU) gene, partial sequence | 217 | 217 | 48.00% | 2.00E-53 | 83.83% | JN941010.1 | |
| 8 | 5 | Phyctochytrium africanum voucher CBS 454.65 28S rRNA gene, partial sequence | 217 | 217 | 48.00% | 2.00E-53 | 83.83% | FJ827083.1 | |
| 9 | 9 | Holtermanniella wattica CBS 9496 28S rRNA gene, partial sequence; from TYPE material | 215 | 215 | 48.00% | 6.00E-53 | 83.61% | NG_058307.1 | |
| 10 | 9 | Holtermanniella wattica culture CBS 9496 large subunit ribosomal RNA gene, partial sequence | 215 | 215 | 48.00% | 6.00E-53 | 83.61% | KY107874.1 | |
| 11 | 11 | Fimicolochytrium alabamea JEL 539 28S rRNA gene, partial sequence; from TYPE material | 213 | 213 | 48.00% | 2.00E-52 | 83.40% | NG_060390.1 | |
| 12 | 11 | Fimicolochytrium alabamei voucher JEL538 28S large subunit ribosomal RNA gene, partial sequence | 213 | 213 | 48.00% | 2.00E-52 | 83.40% | HQ901669.1 | |
| 13 | 11 | Geranomyces semiaquosus BJFC-Gos 18222 28S rRNA gene, partial sequence; from TYPE material | 213 | 213 | 48.00% | 2.00E-52 | 83.62% | NG_042443.1 | |
| 14 | 14 | Carpoceras sp. CLZ-2014 voucher Cui19222 28S large subunit ribosomal RNA gene, partial sequence | 211 | 211 | 48.00% | 6.00E-52 | 83.40% | KF245949.1 | |
| 15 | 14 | Saccomyces raronoi DAOM BR 060 28S rRNA gene, partial sequence; from TYPE material | 211 | 211 | 48.00% | 6.00E-52 | 83.47% | NG_042454.1 | |
| 16 | 17 | Basidioascus undulatus strain CBS 13763 large subunit ribosomal RNA gene, partial sequence | 209 | 209 | 48.00% | 3.00E-51 | 83.19% | MH877552.1 | |
| 17 | 17 | Piskurozyma taiwanensis CBS 9813 28S rRNA gene, partial sequence; from TYPE material | 209 | 209 | 48.00% | 3.00E-51 | 83.19% | NG_058375.1 | |
| 18 | 17 | Goffeauzyma gastrica CBS 2288 28S rRNA gene, partial sequence; from TYPE material | 209 | 209 | 48.00% | 3.00E-51 | 83.19% | NG_058296.1 | |
| 19 | 17 | Goffeauzyma acidotolerans CBS 10872 28S rRNA gene, partial sequence; from TYPE material | 209 | 209 | 48.00% | 3.00E-51 | 83.19% | NG_058295.1 | |
| 20 | 17 | Solicoccozyma aeria culture CBS:155 large subunit ribosomal RNA gene, partial sequence | 209 | 209 | 48.00% | 3.00E-51 | 83.19% | KY109666.1 | |
| 21 | 17 | Piskurozyma taiwanensis culture CBS:9813 large subunit ribosomal RNA gene, partial sequence | 209 | 209 | 48.00% | 3.00E-51 | 83.19% | KY108934.1 | |
| 22 | 17 | Naganishia globosa culture CBS:5106 large subunit ribosomal RNA gene, partial sequence | 209 | 209 | 48.00% | 3.00E-51 | 83.19% | KY108616.1 | |
| 23 | 17 | Naganishia friedmannii culture CBS:7185 large subunit ribosomal RNA gene, partial sequence | 209 | 209 | 48.00% | 3.00E-51 | 83.19% | KY108613.1 | |
| 24 | 17 | Goffeauzyma gastrica culture CBS:2388 large subunit ribosomal RNA gene, partial sequence | 209 | 209 | 48.00% | 3.00E-51 | 83.19% | KY107764.1 | |
| 25 | 17 | Goffeauzyma acidotolerans culture CBS:10872 large subunit ribosomal RNA gene, partial sequence | 209 | 209 | 48.00% | 3.00E-51 | 83.19% | KY107763.1 | |
| 26 | 17 | Filobasidium wieringae culture CBS:1937 large subunit ribosomal RNA gene, partial sequence | 209 | 209 | 48.00% | 3.00E-51 | 83.12% | KY107733.1 | |
| 27 | 17 | Filobasidium magnus culture CBS:140 large subunit ribosomal RNA gene, partial sequence | 209 | 209 | 48.00% | 3.00E-51 | 83.12% | KY107722.1 | |
| 28 | 17 | Filobasidium globisporum culture CBS:7642 large subunit ribosomal RNA gene, partial sequence | 209 | 209 | 48.00% | 3.00E-51 | 83.12% | KY107713.1 | |
| 29 | 17 | Filobasidium floriforme culture CBS:8241 large subunit ribosomal RNA gene, partial sequence | 209 | 209 | 48.00% | 3.00E-51 | 83% | KY107703.1 | |

H9-05-28S_D2G2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Nannochloropsis gaditana strain SAG2.99 28S ribosomal RNA gene, partial sequence | 193 | 193 | 36.00% | 3.00E-46 | 86.00% | FJ030880.1 | Nannochloropsis |
| 2 | 2 | Paraglomus occultum INVAM IA702 28S rRNA gene, partial sequence, from reference material | 187 | 187 | 64.00% | 1.00E-44 | 78.00% | NG_027567.1 | Fungus |
| 3 | 3 | Developayella elegans strain CCAP1917/1 28S ribosomal RNA gene, partial sequence | 183 | 183 | 79.00% | 2.00E-43 | 76.00% | FJ030882.1 | Oomycete |
| 4 | 4 | Saccobolomyces dimmenae genes for LSU rRNA, partial sequence, strain: JCM 8762 | 169 | 169 | 23.00% | 5.00E-39 | 93.00% | AB644404.1 | Fungus |
| 5 | 4 | Saccobolomyces coccideus genes for 18S rRNA, ITS1, 5.8S rRNA, ITS2, 28S rRNA, partial and complete sequence | 169 | 169 | 23.00% | 5.00E-39 | 93.00% | AB838335.1 | Fungus |
| 6 | 6 | Pseudobaeospora wipapatiae SFSU DED B605 28S rRNA gene, partial sequence from TYPE material | 167 | 167 | 33.00% | 2.00E-38 | 86.00% | NG_060108.1 | |
| 7 | 6 | Pseudobaeospora wipapatiae voucher DED B605 28S rRNA gene large subunit ribosomal RNA gene, partial sequence | 167 | 167 | 33.00% | 2.00E-38 | 86.00% | KC464300.1 | |
| 8 | 8 | Afrocastellanos iverysana voucher OSC 150914 28S rRNA gene, partial sequence, from TYPE material | 161 | 161 | 33.00% | 8.00E-37 | 85.00% | NG_058595.1 | |
| 9 | 8 | Afrocastellanos iverysana voucher OSC 150914 28S rRNA gene, partial sequence from TYPE material | 161 | 161 | 33.00% | 8.00E-37 | 85.00% | KX685720.1 | |
| 10 | 8 | Bicorulus dhakarus HKAS 73785 28S rRNA, partial sequence: from TYPE material | 161 | 161 | 33.00% | 8.00E-37 | 85.00% | NG_042663.1 | |
| 11 | 8 | Sporgjiforma squarepantsii voucher LHFB14 28S rRNA gene, partial sequence | 161 | 161 | 33.00% | 8.00E-37 | 85.00% | HQ724500.1 | |
| 12 | 8 | Spongiboma theiliandica HBH DED 7873 28S rRNA, partial sequence from TYPE material | 161 | 161 | 33.00% | 8.00E-37 | 85.00% | NG_042464.1 | |
| 13 | 13 | Minimedusa polyspora strain CBS 113.18 large subunit ribosomal RNA gene, partial sequence | 158 | 158 | 33.00% | 1.00E-35 | 84.00% | MH866167.1 | |
| 14 | 13 | Malassezia equina CBS 9969 28S rRNA gene, partial sequence, from TYPE material | 158 | 158 | 34.00% | 1.00E-35 | 84.00% | NG_060249.1 | |
| 15 | 13 | Phyllozyma linderae CBS 7893 28S rRNA gene, partial sequence from TYPE material | 158 | 158 | 32.00% | 1.00E-35 | 85.00% | NG_058372.1 | |
| 16 | 13 | Phyllozyma coprosmicola CBS 7897 28S rRNA gene, partial sequence, from TYPE material | 158 | 158 | 32.00% | 1.00E-35 | 85.00% | NG_058371.1 | |
| 17 | 13 | Phyllozyma subbrunnea CBS 7196 28S rRNA gene, partial sequence from TYPE material | 158 | 158 | 32.00% | 1.00E-35 | 85.00% | NG_057732.1 | |
| 18 | 13 | Minimedusa polyspora CBS 113.16 28S rRNA gene, partial sequence: from TYPE material | 158 | 158 | 33.00% | 1.00E-35 | 84.00% | NG_057640.1 | |
| 19 | 13 | Phyllozyma subbrunnea culture CBS:7196 large subunit ribosomal RNA gene, partial sequence | 158 | 158 | 32.00% | 1.00E-35 | 85.00% | KY108779.1 | |
| 20 | 13 | Phyllozyma linderae culture CBS:7893 large subunit ribosomal RNA gene, partial sequence | 158 | 158 | 32.00% | 1.00E-35 | 85.00% | KY108777.1 | |
| 21 | 13 | Phyllozyma coprosmicola culture CBS:7897 large subunit ribosomal RNA gene, partial sequence | 158 | 158 | 32.00% | 1.00E-35 | 85.00% | KY108776.1 | |
| 22 | 13 | Minimedusa polyspora gene for 28S rRNA, partial sequence, strain: CBS 113.18 | 158 | 158 | 33.00% | 1.00E-35 | 84.00% | AB972779.1 | |
| 23 | 13 | Malassezia equina strain MA 146 26S rRNA gene, partial sequence | 158 | 158 | 34.00% | 1.00E-35 | 84.00% | AY743621.1 | |
| 24 | 13 | Sporobolomyces subbrunneus isolate AFTOL-ID 893 28S large subunit ribosomal RNA gene, partial sequence | 158 | 158 | 32.00% | 1.00E-35 | 85.00% | AY743711.1 | |
| 25 | 13 | Phyllozyma subbrunnea strain CBS 7196 26S ribosomal RNA gene, partial sequence | 158 | 158 | 32.00% | 1.00E-35 | 85.00% | AF189971.1 | |
| 26 | 13 | Phyllozyma linderae strain CBS 7893 26S ribosomal RNA gene, partial sequence | 158 | 158 | 32.00% | 1.00E-35 | 85.00% | AF189989.1 | |
| 27 | 13 | Phyllozyma coprosmicola strain CBS 7897 26S ribosomal RNA gene, partial sequence | 158 | 158 | 32.00% | 1.00E-35 | 85.00% | AF189981.1 | |
| 28 | 13 | Sporobolomyces linderae 26S ribosomal RNA gene, partial sequence | 158 | 158 | 32.00% | 1.00E-35 | 85.00% | AF207890.1 | |
| 29 | 29 | Hyphen berkeleyanum voucher HO-MEH 17-036 large subunit ribosomal RNA gene, partial sequence | 156 | 156 | 33.00% | 4.00E-35 | 85.00% | MG772970.1 | |
| 30 | 29 | Cacestrum verrucosomaiossum INPA 264956 28S rRNA gene, partial sequence: from TYPE material | 156 | 156 | 33.00% | 4.00E-35 | 84.00% | NG_060680.1 | |
| 31 | 29 | Clavulina cessea URM 89970 28S rRNA gene, partial sequence from TYPE material | 156 | 156 | 32.00% | 4.00E-35 | 84.81% | NG_058857.1 | |
| 32 | 29 | Clavulina cessea culture URM:BRA:x89970 large subunit ribosomal RNA gene, partial sequence | 156 | 156 | 32.00% | 4.00E-35 | 84.81% | KX811197.1 | |
| 33 | 29 | Cacestrum verrucosomaiossum voucher INPA2649656 28S ribosomal RNA gene, partial sequence | 156 | 156 | 32.00% | 4.00E-35 | 84.38% | KX670931.1 | |
| 34 | 29 | Borrelia flavopermilina strain JL192-01 28S large subunit ribosomal RNA gene, partial sequence | 156 | 156 | 32.00% | 4.00E-35 | 84.91% | DQ915469.1 | |

Fig.17

H9-05-28S_D2R2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Chlorellidium tetrabotrys strain SAG811-1 28S ribosomal RNA gene, partial sequence | 215 | 215 | 48.00% | 6.00E-53 | 84.21% | FJ830891.1 | Yellow-green algae |
| 2 | 2 | Fimicolochytrium jonesii JEL569 28S rRNA gene, partial sequence, from TYPE material | 206 | 206 | 48.00% | 4.00E-50 | 83.56% | NG_060391.1 | Fungus |
| 3 | 2 | Fimicolochytrium jonesii voucher JEL569 28S large subunit ribosomal RNA gene, partial sequence | 206 | 206 | 48.00% | 4.00E-50 | 83.56% | HQ901661.1 | Fungus |
| 4 | 4 | Geranomyces variabilis voucher MP03 28S large subunit ribosomal RNA gene, partial sequence | 200 | 200 | 48.00% | 2.00E-48 | 83.33% | HQ901692.1 | Fungus |
| 5 | 5 | Thoreauomyces humboldtii JEL95 28S rRNA gene, partial sequence, from TYPE material | 198 | 198 | 48.00% | 7.00E-48 | 83.19% | NG_059938.1 | Fungus |
| 6 | 5 | Thoreauomyces humboldtii voucher JEL95 28S large subunit ribosomal RNA gene, partial sequence | 198 | 198 | 48.00% | 7.00E-48 | 83.19% | HQ901662.1 | |
| 7 | 5 | Spizellomyces acuminatus 28S ribosomal RNA (LSU) gene, partial sequence | 198 | 198 | 48.00% | 7.00E-48 | 83.11% | JN411010.1 | |
| 8 | 5 | Phlyctochytrium africanum voucher CBS 484.65 28S ribosomal RNA gene, partial sequence | 198 | 198 | 48.00% | 7.00E-48 | 83.11% | FJ827693.1 | |
| 9 | 9 | Holtermanniella wattica CBS 9496 28S rRNA gene, partial sequence, from TYPE material | 196 | 196 | 48.00% | 2.00E-47 | 82.99% | NG_058307.1 | |
| 10 | 9 | Holtermanniella wattica culture JEL 538 28S large subunit ribosomal RNA gene, partial sequence | 196 | 196 | 48.00% | 2.00E-47 | 82.89% | KY107814.1 | |
| 11 | 11 | Fimicolochytrium alabamae JEL538 28S rRNA gene, partial sequence, from TYPE material | 195 | 195 | 48.00% | 8.00E-47 | 82.67% | NG_060390.1 | |
| 12 | 11 | Gorgonomyces haynaldii BAFC ARG 026 28S rRNA gene, partial sequence, from TYPE material | 195 | 195 | 47.00% | 8.00E-47 | 83.11% | NG_042448.1 | |
| 13 | 13 | Conoplasta semispora BJFC Cui 10222 28S rRNA gene, partial sequence, from TYPE material | 193 | 193 | 48.00% | 3.00E-46 | 82.68% | NG_064354.1 | |
| 14 | 14 | Cercozoasis sp. CLZ-2014 voucher Cui 10222 28S large subunit ribosomal RNA gene, partial sequence | 193 | 193 | 48.00% | 3.00E-46 | 82.65% | KF345949.1 | |
| 15 | 14 | Sorosraphlyctis ramzzesii DAOM BR 060 28S rRNA gene, partial sequence, from TYPE material | 193 | 193 | 48.00% | 3.00E-46 | 82.74% | NG_042454.1 | |
| 16 | 14 | Basidiascus undulatus strain CBS 9813 28S rRNA gene, partial sequence | 193 | 193 | 48.00% | 3.00E-46 | 82.46% | MH877552.1 | |
| 17 | 17 | Pichuracyma taiwaensis CBS 10872 28S rRNA gene, partial sequence, from TYPE material | 191 | 191 | 48.00% | 1.00E-45 | 82.46% | NG_056175.1 | |
| 18 | 17 | Goffeauzyma gastrica CBS 2288 28S rRNA gene, partial sequence, from TYPE material | 191 | 191 | 48.00% | 1.00E-45 | 82.46% | NG_058296.1 | |
| 19 | 17 | Goffeauzyma acidolerans CBS 10872 28S rRNA gene, partial sequence, from TYPE material | 191 | 191 | 48.00% | 1.00E-45 | 82.46% | NG_058295.1 | |
| 20 | 17 | Goffeauzyma aeria culture CBS 155 28S large subunit ribosomal RNA gene, partial sequence | 191 | 191 | 48.00% | 1.00E-45 | 82.46% | KY109860.1 | |
| 21 | 17 | Pichuracyma taiwaensis culture CBS 9813 large subunit ribosomal RNA gene, partial sequence | 191 | 191 | 48.00% | 1.00E-45 | 82.46% | KY108934.1 | |
| 22 | 17 | Pichuracyma cylindrica culture CBS 8680 large subunit ribosomal RNA gene, partial sequence | 191 | 191 | 48.00% | 1.00E-45 | 82.46% | KY108932.1 | |
| 23 | 17 | Naganishia globosa culture CBS 5106 large subunit ribosomal RNA gene, partial sequence | 191 | 191 | 48.00% | 1.00E-45 | 82.46% | KY108814.1 | |
| 24 | 17 | Naganishia friedmanni culture CBS 7160 large subunit ribosomal RNA gene, partial sequence | 191 | 191 | 48.00% | 1.00E-45 | 82.46% | KY108813.1 | |
| 25 | 17 | Goffeauzyma gastrica culture CBS 2288 large subunit ribosomal RNA gene, partial sequence | 191 | 191 | 48.00% | 1.00E-45 | 82.46% | KY107764.1 | |
| 26 | 17 | Goffeauzyma acidolerans culture CBS 10872 large subunit ribosomal RNA gene, partial sequence | 191 | 191 | 48.00% | 1.00E-45 | 82.46% | KY107763.1 | |
| 27 | 17 | Filobasidium wieringae culture CBS 1937 large subunit ribosomal RNA gene, partial sequence | 191 | 191 | 48.00% | 1.00E-45 | 82.35% | KY107733.1 | |
| 28 | 17 | Filobasidium magnum culture CBS 140 large subunit ribosomal RNA gene, partial sequence | 191 | 191 | 48.00% | 1.00E-45 | 82.35% | KY107722.1 | |
| 29 | 17 | Filobasidium globisporum culture CBS 7642 large subunit ribosomal RNA gene, partial sequence | 191 | 191 | 48.00% | 1.00E-45 | 82.38% | KY107713.1 | |
| 30 | 17 | Filobasidium floriforme culture CBS 6241 large subunit ribosomal RNA gene, partial sequence | 191 | 191 | 48.00% | 1.00E-45 | 82.38% | KY107703.1 | |
| 31 | 17 | Filobasidium floriforme culture CBS 6241 large subunit ribosomal RNA gene, partial sequence | 191 | 191 | 48.00% | 1.00E-45 | 82.46% | KY106881.1 | |
| 32 | 17 | Cryptococcus terreitis culture CBS 7159 large subunit ribosomal RNA gene, partial sequence | 191 | 191 | 48.00% | 1.00E-45 | 82.46% | KY106881.1 | |
| 33 | 17 | Cryptococcus albidus var. ovalis culture CBS 5810 large subunit ribosomal RNA gene, partial sequence | 191 | 191 | 48.00% | 1.00E-45 | 82.46% | KY106965.1 | |
| 34 | 17 | Cryptococcus albidus var. kuetzengii culture CBS 1926 large subunit ribosomal RNA gene, partial sequence | 191 | 191 | 48.00% | 1.00E-45 | 82.46% | KY106960.1 | |
| 35 | 17 | Gemmibasidium kerahum DAOM 241869 28S rRNA gene, partial sequence, from TYPE material | 191 | 191 | 48.00% | 1.00E-45 | 82.46% | NG_042695.1 | |
| 36 | 17 | Gemmibasidium donium DAOM 241848 28S rRNA gene, partial sequence, from TYPE material | 191 | 191 | 48.00% | 1.00E-45 | 82.46% | NG_042694.1 | |
| 37 | 17 | Basidioascus magnus DAOM 241966 28S rRNA gene, partial sequence, from TYPE material | 191 | 191 | 48.00% | 1.00E-45 | 82.46% | NG_042693.1 | |
| 38 | 17 | Basidioascus undulatus DAOM 241956 28S rRNA gene, partial sequence, from TYPE material | 191 | 191 | 48.00% | 1.00E-45 | 82.46% | NG_042692.1 | |

H9-08-28S D2C2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Nannochloropsis gaditana strain SAG2.98 28S ribosomal RNA gene, partial sequence | 189 | 189 | 40.00% | 3.00E-45 | 86.00% | FJ030660.1 | Nannochloropsis |
| 2 | 2 | Developayella elegans strain CCAP1917/1 28S ribosomal RNA gene, partial sequence | 172 | 172 | 59.00% | 3.00E-40 | 79.00% | FJ030682.1 | Oomycete |
| 3 | 3 | Sporobolomyces dimmenae gene for LSU rRNA, partial sequence, strain: JCM 8762 | 169 | 169 | 26.00% | 4.00E-39 | 93.00% | AB644404.1 | Fungus |
| 4 | 3 | Sporobolomyces coralliae genes for 18S rRNA, ITS1, 5.8S rRNA, ITS2, 28S rRNA, partial and complete sequence | 169 | 169 | 26.00% | 4.00E-39 | 93.00% | AB638335.1 | Fungus |
| 5 | 5 | Paraglomus occultum IRVAM IA702 26S rRNA gene, partial sequence, from reference material | 167 | 167 | 41.00% | 2.00E-38 | 83.00% | NG_027567.1 | Fungus |
| 6 | 6 | Pseudobaeospora vesparium isolate SFSU DED 8605 28S rRNA gene, partial sequence, from TYPE material | 163 | 163 | 25.00% | 2.00E-37 | 93.00% | NG_060108.1 | |
| 7 | 6 | Pseudobaeospora vesparium voucher DED 8605 28S large subunit ribosomal RNA gene, partial sequence | 163 | 163 | 25.00% | 2.00E-37 | 93.00% | KCA64330.1 | |
| 8 | 8 | Afrocastellania ivoryana OSC 150014 28S rRNA gene, partial sequence, from TYPE material | 158 | 158 | 25.00% | 1.00E-35 | 92.00% | NG_058595.1 | |
| 9 | 8 | Afrocastellania ivoryana voucher OSC 150014 28S rRNA gene, partial sequence | 158 | 158 | 25.00% | 1.00E-35 | 92.00% | KX685720.1 | |
| 10 | 8 | Bacrofutus dhakanus HKAS 73785 28S rRNA gene, partial sequence, from TYPE material | 158 | 158 | 25.00% | 1.00E-35 | 92.00% | NG_042663.1 | |
| 11 | 8 | Spongiforma squarepantsii voucher LHFB14 28S rRNA gene, partial sequence | 158 | 158 | 25.00% | 1.00E-35 | 92.00% | HQ224309.1 | |
| 12 | 8 | Spongiforma thailandica BBH DED 7173 28S rRNA gene, partial sequence, from TYPE material | 158 | 158 | 25.00% | 1.00E-35 | 92.00% | NG_042464.1 | |
| 13 | 13 | Phyllozyma linderae CBS 7893 28S rRNA gene, partial sequence, from TYPE material | 156 | 156 | 25.00% | 3.00E-35 | 92.00% | NG_058372.1 | |
| 14 | 13 | Phyllozyma coprosmicola CBS 7897 28S rRNA gene, partial sequence, from TYPE material | 156 | 156 | 25.00% | 3.00E-35 | 92.00% | NG_058371.1 | |
| 15 | 13 | Phyllozyma subbrunnea CBS 7196 28S rRNA gene, partial sequence, from TYPE material | 156 | 156 | 25.00% | 3.00E-35 | 92.00% | NG_057732.1 | |
| 16 | 13 | Phyllozyma subbrunnea culture CBS:7196 large subunit ribosomal RNA gene, partial sequence | 156 | 156 | 25.00% | 3.00E-35 | 92.00% | KY108779.1 | |
| 17 | 13 | Phyllozyma linderae culture CBS:7893 large subunit ribosomal RNA gene, partial sequence | 156 | 156 | 25.00% | 3.00E-35 | 92.00% | KY108777.1 | |
| 18 | 13 | Phyllozyma coprosmicola culture CBS:7897 large subunit ribosomal RNA gene, partial sequence | 156 | 156 | 25.00% | 3.00E-35 | 92.00% | KY108776.1 | |
| 19 | 13 | Sporobolomyces subbrunneus isolate AFTOL-ID 848 28S large subunit ribosomal RNA gene, partial sequence | 156 | 156 | 25.00% | 3.00E-35 | 92.00% | AY745171.1 | |
| 20 | 13 | Phyllozyma subbrunnea strain CBS 7196 26S ribosomal RNA gene, partial sequence | 156 | 156 | 25.00% | 3.00E-35 | 92.00% | AF189997.1 | |
| 21 | 13 | Phyllozyma linderae strain CBS 7893 26S ribosomal RNA gene, partial sequence | 156 | 156 | 25.00% | 3.00E-35 | 92.00% | AF189989.1 | |
| 22 | 13 | Phyllozyma coprosmicola strain CBS 7897 28S ribosomal RNA gene, partial sequence | 156 | 156 | 25.00% | 3.00E-35 | 92.00% | AF189981.1 | |
| 23 | 13 | Sporobolomyces linderae 26S ribosomal RNA gene, partial sequence | 156 | 156 | 25.00% | 3.00E-35 | 92.00% | AF207890.1 | |
| 24 | 24 | Minimedusa polyspora strain CBS 113.16 26S rRNA gene, partial sequence, from TYPE material | 154 | 154 | 25.00% | 1.00E-34 | 91.00% | MH866167.1 | |
| 25 | 24 | Hydnum berkeleyanum voucher KO-MEH 17-069 large subunit ribosomal RNA gene, partial sequence | 154 | 154 | 25.00% | 1.00E-34 | 91.00% | MG972970.1 | |
| 26 | 24 | Geastrum verrucoramulosum voucher INPA 264956 28S rRNA gene, partial sequence, from TYPE material | 154 | 154 | 25.00% | 1.00E-34 | 91.00% | NG_060850.1 | |
| 27 | 24 | Malassezia equina CBS 9969 28S rRNA gene, partial sequence, from TYPE material | 154 | 154 | 37.00% | 1.00E-34 | 84.00% | NG_060248.1 | |
| 28 | 24 | Clavulina ossea URM 89970 28S rRNA gene, partial sequence, from TYPE material | 154 | 154 | 25.00% | 1.00E-34 | 91.00% | NG_060957.1 | |
| 29 | 24 | Anthracoidea rothenbachii KRA F-2012-148 28S rRNA gene, partial sequence, from TYPE material | 154 | 154 | 25.00% | 1.00E-34 | 92.00% | NG_058781.1 | |
| 30 | 24 | Minimedusa polyspora CBS 113.16 28S rRNA gene, partial sequence, from TYPE material | 154 | 154 | 25.00% | 1.00E-34 | 91.00% | NG_057840.1 | |
| 31 | 24 | Clavulina ossea culture URM(BRA)>89970 large subunit ribosomal RNA gene, partial sequence | 154 | 154 | 25.00% | 1.00E-34 | 91.15% | KX811197.1 | |
| 32 | 24 | Geastrum verrucoramulosum voucher INPA:264956 26S ribosomal RNA gene, partial sequence | 154 | 154 | 25.00% | 1.00E-34 | 91.15% | KX670831.1 | |
| 33 | 24 | Anthracoidea pannosoides voucher KRA large subunit ribosomal RNA gene, partial sequence | 154 | 154 | 25.00% | 1.00E-34 | 91.62% | KT006854.1 | |
| 34 | 24 | Minimedusa polyspora gene for 26S rRNA, partial sequence, strain: CBS 113.16 | 154 | 154 | 25.00% | 1.00E-34 | 91.15% | AB972779.1 | |
| 35 | 24 | Bursella flavogemmulosa 26S large subunit ribosomal RNA gene, partial sequence | 154 | 154 | 25.00% | 1.00E-34 | 91.15% | DQ915469.1 | |
| 36 | 24 | Malassezia equina strain MA 146 26S ribosomal RNA gene, partial sequence | 154 | 154 | 37.00% | 1.00E-34 | 83.64% | AY743621.1 | |

H9-09-18S
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Pedospumella encystans voucher B 40 180A0671 18S ribosomal RNA gene, partial sequence | 1170 | 1427 | 93.00% | 0 | 89.00% | AY651083.1 | Golden algae |
| 2 | 2 | Spumella vulgaris isolate 199hm 18S ribosomal RNA gene, partial sequence | 1120 | 1370 | 92.00% | 0 | 89.00% | DQ380552.1 | Golden algae |
| 3 | 3 | Streptofilum capillatum strain SAG 2559 small subunit ribosomal RNA gene, partial sequence | 1114 | 1346 | 93.00% | 0 | 88.00% | MG652626.1 | Charophytes |
| 4 | 4 | Fistulifera solaris gene for 18S ribosomal RNA, partial sequence | 1112 | 1350 | 93.00% | 0 | 88.00% | AB769957.1 | Diatom |
| 5 | 4 | Eustigmatos vischeri isolate SAG 860-1 18S ribosomal RNA gene, complete sequence | 1112 | 1365 | 93.00% | 0 | 88.00% | JX274590.1 | Nannochloropsis |
| 6 | 4 | Eustigmatos polyphem strain SAG 38.84 18S ribosomal RNA gene, complete sequence | 1112 | 1365 | 93.00% | 0 | 88.00% | JX188077.1 | Nannochloropsis |
| 7 | 4 | Vischeria helvetica strain SAG 876-1 18S ribosomal RNA gene, complete sequence | 1112 | 1359 | 93.00% | 0 | 88.00% | JX188080.1 | |
| 8 | 8 | Pseudotetraebdela karsteliae strain SAG 2056 18S ribosomal RNA gene, partial sequence | 1109 | 1359 | 93.00% | 0 | 88.00% | EF044311.1 | |
| 9 | 9 | Monodus unipapilla partial 18S rRNA gene, strain SAG 8.83 | 1109 | 1359 | 93.00% | 0 | 88.00% | AM490621.1 | |
| 10 | 10 | Heterococcus fuornensis partial 18S rRNA gene, strain SAG 835-5 | 1101 | 1352 | 92.00% | 0 | 88.00% | AM490621.1 | |
| 11 | 10 | Heterococcus caespitosus partial 18S rRNA gene, strain SAG 835-2a | 1101 | 1352 | 92.00% | 0 | 88.00% | AM490820.1 | |
| 12 | 10 | Nannochloropsis limnetica strain SAG 18.99 culture collection SAG 18.99 18S ribosomal RNA gene, partial sequence | 1101 | 1346 | 95.00% | 0 | 87.00% | AF251496.1 | |
| 13 | 13 | Clipidopsis heterosiphoniae isolate KMJ-M-arca4 18S ribosomal RNA gene, partial sequence | 1099 | 1342 | 91.00% | 0 | 88.00% | MF808767.1 | |
| 14 | 13 | Saitoella complicata strain NRRL Y-17804 18S rRNA gene, partial sequence | 1099 | 1309 | 93.00% | 0 | 88.00% | JQ698935.1 | |
| 15 | 13 | Saitoella complicata IAM 12963 18S rRNA gene, partial sequence; from TYPE material | 1099 | 1309 | 93.00% | 0 | 88.00% | NG_013154.1 | |
| 16 | 13 | Peterosupumella lacustris voucher B 40 00A0673 18S ribosomal RNA gene, partial sequence | 1088 | 1329 | 92.00% | 0 | 88.00% | AY651074.1 | |
| 17 | 13 | Chlorellidium tetrabotrys strain SAG811-1 18S ribosomal RNA gene, partial sequence | 1086 | 1357 | 92.00% | 0 | 88.00% | FJ030892.1 | |
| 18 | 18 | Saitoella complicata gene for 18S rRNA | 1086 | 1313 | 92.00% | 0 | 88.00% | D12530.1 | |
| 19 | 19 | Ochromonas danica strain SAG933.7 18S rRNA gene, partial sequence | 1086 | 1315 | 92.00% | 0 | 88.00% | JQ281514.1 | |
| 20 | 20 | Hydurospbdium curvatum SAG 235-1 18S rRNA gene, partial sequence; from reference material | 1077 | 1304 | 93.00% | 0 | 88.00% | NG_017172.1 | |
| 21 | 21 | Micromonas commoda isolate RCC299 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1074 | 1311 | 92.00% | 0 | 88.00% | KU612123.1 | |
| 22 | 21 | Micromonas sp. RCC299 18S ribosomal RNA gene, partial sequence | 1074 | 1311 | 92.00% | 0 | 88.00% | HM191693.1 | |
| 23 | 21 | Micromonas sp. RCC299 chromosome 8, complete sequence | 1074 | 3934 | 92.00% | 0 | 88.00% | CP001575.1 | |
| 24 | 21 | Sphaerosorus compasta partial 18S rRNA gene, strain SAG 53.91 | 1074 | 1329 | 92.00% | 0 | 88.00% | AJ579333.1 | |
| 25 | 25 | Taphrina populina CBS 337.55 18S rRNA gene, partial sequence; from TYPE material | 1070 | 1261 | 92.00% | 0 | 87.00% | NG_062683.1 | |
| 26 | 25 | Taphrina populina gene for 18S rRNA | 1070 | 1261 | 92.00% | 0 | 87.00% | D14161.1 | |
| 27 | 27 | Endogone corticoides gene for 18S ribosomal RNA, partial sequence, specimen_voucher A-14052 | 1069 | 1270 | 85.00% | 0 | 88.00% | LC107355.1 | |
| 28 | 27 | Micromonas commoda 18S ribosomal RNA gene, partial sequence | 1069 | 1300 | 92.00% | 0 | 87.00% | KU244632.1 | |
| 29 | 27 | Klebsormidium elegans 18S rRNA gene, 5.8S rRNA gene, ITS2 and 26S rRNA gene (partial), strain SAG 7.96 | 1068 | 1297 | 93.00% | 0 | 87.00% | AM490840.1 | |
| 30 | 27 | Klebsormidium dissectum strain SAG 2155 18S ribosomal RNA gene, partial sequence; internal transcribed spacer 1, 5.8S ribosomal RNA gene, and internal transcribed spacer 2, complete sequence; and 26S ribosomal RNA gene, partial sequence | 1068 | 1291 | 93.00% | 0 | 87.00% | EF372518.1 | |

H9-09-28S_D2R2
Search condition: Limit to sequences from type material

| | Description | Max score | Total score | Query cover | E value | Ident | Accession | |
|---|---|---|---|---|---|---|---|---|
| 1 | Chlorellidium tetrabotrys strain SAG811-1 28S ribosomal RNA gene, partial sequence | 196 | 196 | 50.00% | 2.00E-47 | 82.00% | FJ030881.1 | Yellow-green algae |
| 2 | Cercospora sp. CLZ-2014 voucher Cu 19222 28S large subunit ribosomal RNA gene, partial sequence | 185 | 185 | 50.00% | 4.00E-44 | 81.00% | KF845849.1 | Fungus |
| 3 | Spizellomyces acuminatus 28S ribosomal RNA (LSU) gene, partial sequence | 183 | 183 | 50.00% | 1.00E-43 | 81.00% | JN941010.1 | Fungus |
| 4 | Rhizoclosmatium africanum voucher CBS 454.65 28S ribosomal RNA gene, partial sequence | 183 | 183 | 50.00% | 1.00E-43 | 81.00% | FJ827693.1 | Fungus |
| 5 | Fimicolochytrium jonesii JEL 569 28S rRNA gene, partial sequence; from TYPE material | 182 | 182 | 50.00% | 5.00E-43 | 81.00% | NG_060391.1 | Fungus |
| 6 | Geranomyces variabilis voucher MP03 28S large subunit ribosomal RNA gene, partial sequence | 182 | 182 | 50.00% | 5.00E-43 | 81.00% | HQ901692.1 | |
| 7 | Fimicolochytrium jonesii voucher JEL569 28S large subunit ribosomal RNA gene, partial sequence | 182 | 182 | 50.00% | 5.00E-43 | 81.00% | HQ901681.1 | |
| 8 | Thoreauomyces humboldtii JEL 85 28S rRNA gene, partial sequence; from TYPE material | 180 | 180 | 50.00% | 2.00E-42 | 81.00% | NG_059936.1 | |
| 9 | Thoreauomyces humboldtii voucher JEL85 28S large subunit ribosomal RNA gene, partial sequence | 180 | 180 | 50.00% | 2.00E-42 | 81.00% | HQ901662.1 | |
| 10 | Sonoraphlyctis ranzonii DAOM BR 060 28S rRNA, partial sequence; from TYPE material | 180 | 180 | 50.00% | 2.00E-42 | 81.00% | NG_042454.1 | |
| 11 | Basidiascus undulatus strain CBS 135783 28S large subunit ribosomal RNA gene, partial sequence | 178 | 178 | 50.00% | 6.00E-42 | 80.00% | MH877552.1 | |
| 12 | Piakurozyma taiwanensis CBS 9813 28S rRNA gene, partial sequence; from TYPE material | 178 | 178 | 50.00% | 6.00E-42 | 80.00% | NG_058375.1 | |
| 13 | Goffeauzyma aciditolerans CBS 10872 28S rRNA gene, partial sequence; from TYPE material | 178 | 178 | 50.00% | 6.00E-42 | 80.00% | NG_058295.1 | |
| 14 | Solicoccozyma terrea culture CBS:1155 large subunit ribosomal RNA gene, partial sequence | 178 | 178 | 50.00% | 6.00E-42 | 80.00% | KY109866.1 | |
| 15 | Piakurozyma taiwanensis culture CBS:9813 large subunit ribosomal RNA gene, partial sequence | 178 | 178 | 50.00% | 6.00E-42 | 80.00% | KY108934.1 | |
| 16 | Piskurozyma cylindrica culture CBS:8680 large subunit ribosomal RNA gene, partial sequence | 178 | 178 | 50.00% | 6.00E-42 | 80.00% | KY108932.1 | |
| 17 | Naganishia globosa culture CBS:5106 large subunit ribosomal RNA gene, partial sequence | 178 | 178 | 50.00% | 6.00E-42 | 80.00% | KY108616.1 | |
| 18 | Naganishia friedmannii culture CBS:7160 large subunit ribosomal RNA gene, partial sequence | 178 | 178 | 50.00% | 6.00E-42 | 80.00% | KY108613.1 | |
| 19 | Goffeauzyma aciditolerans culture CBS:10872 large subunit ribosomal RNA gene, partial sequence | 178 | 178 | 50.00% | 6.00E-42 | 80.00% | KY107783.1 | |
| 20 | Filobasidium wieringae culture CBS:1937 large subunit ribosomal RNA gene, partial sequence | 178 | 178 | 50.00% | 6.00E-42 | 80.00% | KY107733.1 | |
| 21 | Filobasidium magnum culture CBS:140 large subunit ribosomal RNA gene, partial sequence | 178 | 178 | 50.00% | 6.00E-42 | 80.00% | KY107722.1 | |
| 22 | Filobasidium globisporum culture CBS:7642 large subunit ribosomal RNA gene, partial sequence | 178 | 178 | 50.00% | 6.00E-42 | 80.00% | KY107713.1 | |
| 23 | Filobasidium floriforme culture CBS:6241 large subunit ribosomal RNA gene, partial sequence | 178 | 178 | 50.00% | 6.00E-42 | 80.00% | KY107703.1 | |
| 24 | Cryptococcus consortionis culture CBS:7159 large subunit ribosomal RNA gene, partial sequence | 178 | 178 | 50.00% | 6.00E-42 | 80.00% | KY106981.1 | |
| 25 | Cryptococcus skinneri var. skinneri culture CBS:5810 large subunit ribosomal RNA gene, partial sequence | 178 | 178 | 50.00% | 6.00E-42 | 80.00% | KY106985.1 | |
| 26 | Cryptococcus skinneri var. skinneri culture CBS:1926 large subunit ribosomal RNA gene, partial sequence | 178 | 178 | 50.00% | 6.00E-42 | 80.00% | KY106960.1 | |
| 27 | Geminibasidium hirsutum DACM 241969 28S rRNA, partial sequence; from TYPE material | 178 | 178 | 50.00% | 6.00E-42 | 80.00% | NG_042695.1 | |
| 28 | Geminibasidium donsium DACM 241966 28S rRNA, partial sequence; from TYPE material | 178 | 178 | 50.00% | 6.00E-42 | 80.00% | NG_042694.1 | |
| 29 | Basidioascus magus DACM 241345 28S rRNA, partial sequence; from TYPE material | 178 | 178 | 50.00% | 6.00E-42 | 80.00% | NG_042693.1 | |
| 30 | Basidioascus undulatus DACM 241968 28S rRNA, partial sequence; from TYPE material | 178 | 178 | 50.00% | 6.00E-42 | 80.00% | NG_042692.1 | |

METHOD FOR PRODUCING 3,5-DIHYDROXY-4-METHOXYBENZYL ALCOHOL FROM PLANKTON

TECHNICAL FIELD

The present invention relates to a method for producing 3,5-dihydroxy-4-methoxybenzyl alcohol, the method producing 3,5-dihydroxy-4-methoxybenzyl alcohol serving as an antioxidant from plankton.

BACKGROUND ART

The present inventor has already found a novel antioxidant, 3,5-dihydroxy-4-methoxybenzyl alcohol (hereinafter referred to as "DHMBA"), in heated oyster meat and also succeeded in synthesizing and identifying this substance. Note that DHMBA is not detected in raw oyster meat.

Regarding this matter, it is generally known that, as a biological characteristic of oyster, oyster draws a large quantity of seawater, thereby digestively obtaining plankton as a feed from the large quantity of seawater thus drawn.

CITATION LIST

Patent Literature

Patent Literature 1: JP 2016-42825 A

SUMMARY OF INVENTION

Technical Problem

Thus, in the present invention, the present inventor built a hypothesis that DHMBA was included in the plankton.

First, DHMBA in the plankton was measured by collecting and filtering the plankton only to find that DHMBA was not detected. Next, when the plankton were collected, filtered, and heated, DHMBA was detected. Further, when the plankton were collected, filtered, and pressurized, DHMBA was detected.

Thus, the present inventor contemplated that the aforementioned DHMBA was a useful substance derived from the plankton and therefore invented a method for producing DHMBA from the plankton.

Solution to Problem

The present invention includes filtering collected seawater containing plankton using a filter, taking out a cell content from the plankton remained on the filter, and then heating the cell content thus taken out to produce 3,5-dihydroxy-4-methoxybenzyl alcohol from a heated material thus heated, wherein the plankton is a diatom.

Alternatively, the present invention includes filtering collected seawater containing plankton using a filter, taking out a cell content from the plankton remained on the filter, and then heating the cell content thus taken out to produce 3,5-dihydroxy-4-methoxybenzyl alcohol from a heated material thus heated, wherein the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

Alternatively, the present invention includes filtering collected seawater containing plankton using a filter, crushing the plankton remained on the filter with an addition of an extracting solution, and extracting a cell content from the plankton followed by heating to produce 3,5-dihydroxy-4-methoxybenzyl alcohol from a heated material thus heated, wherein the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

Alternatively, in the present invention, the heating time is at least 1 hour or longer.

Alternatively, the present invention includes filtering collected seawater containing plankton using a filter, taking out a cell content from the plankton remained on the filter, and then pressurizing the cell content thus taken out to produce 3,5-dihydroxy-4-methoxybenzyl alcohol from a pressurized material thus pressurized, wherein the plankton is a diatom.

Alternatively, the present invention includes filtering collected seawater containing plankton using a filter, taking out a cell content from the plankton remained on the filter, and then pressurizing the cell content thus taken out to produce 3,5-dihydroxy-4-methoxybenzyl alcohol from a pressurized material thus pressurized, wherein the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

Alternatively, the present invention includes filtering collected seawater containing plankton using a filter, crushing the plankton remained on the filter with an addition of an extracting solution, and extracting a cell content from the plankton followed by pressurization to produce 3,5-dihydroxy-4-methoxybenzyl alcohol from a pressurized material thus pressurized, wherein the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

Alternatively, in the present invention, the pressurization is performed at at least 2 atmospheres or more.

Alternatively, in the present invention, the pressurizing time is at least 1 hour or longer.

Advantageous Effects of Invention

The present invention can provide the method for producing the antioxidant DHMBA from the plankton included in the seawater by collecting the seawater including the plankton, thereby achieving excellent advantageous effects.

BRIEF DESCRIPTION OF DRAWINGS

FIG. 9 is an explanatory diagram (2) illustrating the global search result under the search condition excluding the environmental sequences.

FIG. 10 is an explanatory diagram (1) illustrating the search result under the search condition in which the search is limited to sequences from type material.

FIG. 11 is an explanatory diagram (2) illustrating the search result under the search condition in which the search is limited to the sequences from type material.

FIG. 13 is an explanatory diagram (4) illustrating the global search result under the search condition excluding the environmental sequences.

FIG. 15 is an explanatory diagram (3) illustrating the search result under the search condition in which the search is limited to the sequences from type material.

FIG. 16 is an explanatory diagram (4) illustrating the search result under the search condition in which the search is limited to the sequences from type material.

FIG. 17 is an explanatory diagram (5) illustrating the search result under the search condition in which the search is limited to the sequences from type material.

FIG. 20 is an explanatory diagram (8) illustrating the global search result under the search condition excluding the environmental sequences.

FIG. 21 is an explanatory diagram (6) illustrating the search result under the search condition in which the search is limited to the sequences from type material.

FIG. 22 is an explanatory diagram (7) illustrating the search result under the search condition in which the search is limited to the sequences from type material.

FIG. 23 is an explanatory diagram (8) illustrating the search result under the search condition in which the search is limited to the sequences from type material.

FIG. 26 is an explanatory diagram (11) illustrating the global search result under the search condition excluding the environmental sequences.

FIG. 27 is an explanatory diagram (9) illustrating the search result under the search condition in which the search is limited to the sequences from type material.

FIG. 28 is an explanatory diagram (10) illustrating the search result under the search condition in which the search is limited to the sequences from type material.

FIG. 29 is an explanatory diagram (11) illustrating the search result under the search condition in which the search is limited to the sequences from type material.

DESCRIPTION OF EMBODIMENTS

First, the seawater was collected in a sea area where oyster farming was primarily performed (e.g., sea areas in Hiroshima and Miyagi, Japan) at a predetermined period and the collected seawater was filtered to take out plankton 1 remained on a filter used for filtration. The plankton 1 were heated or pressurized and then subjected to examination and analysis to determine whether or not DHMBA was detected.

First, detection of DHMBA after heating will be described. The seawater was collected in an actual sea area where oyster farming was performed (e.g., sea areas in Hiroshima and Miyagi, Japan).

(Collection of Seawater Including Plankton)

The seawater is pumped up by a pump or the like in the sea area where oyster farming is performed (e.g., the sea areas in Hiroshima and Miyagi, Japan) at a predetermined period. Specifically, the seawater including the plankton is pumped up in the sea area in Hiroshima in September and March and in the sea area in Miyagi in May.

Note that, in the present example, the seawater in the sea areas in Hiroshima and Miyagi was collected. However, the invention is not limited to the seawater in Hiroshima and Miyagi.

Further, regarding the period, the invention is not limited to the seawater in September or March.

(Filtration of Seawater Including Plankton)

Figure 1:
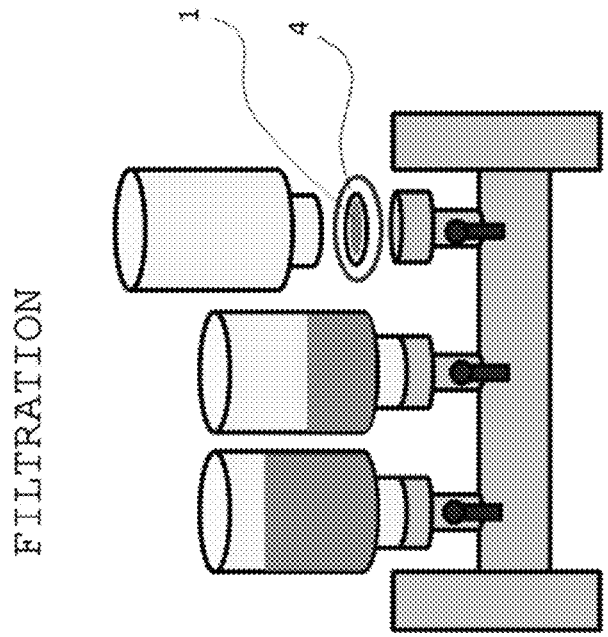
FIG. 1 is an explanatory diagram illustrating filtration of collected seawater.

The seawater including the plankton 1 was collected and then filtrated through a filter formed of a nonwoven fabric or the like, for example, a GF/C filter 4 (see FIG. 1).

In this operation, the amount of the seawater to be filtered was not limited. This time, about 3100 liters of seawater was collected in each sea area in Hiroshima and Miyagi and filtered through the filter.

Note that the filter used for filtration in the above method has a large amount of the plankton 1 adhered thereon, and the filter on which the plankton 1 are adhered can be frozen and stored until an extraction operation is performed.

(Ultrasonic Treatment)

Next, for example, in a case where the filter on which the plankton 1 are adhered is frozen and stored, the filter which is frozen and stored is put into a container 5 such as a centrifuge tube, the container 5 is filled with, for example, ultrapure water, and the plankton 1 are further subjected to, for example, sonication using ultrasonic waves for about 1 hour or a ball mill treatment to destroy cell walls, thereby facilitating extraction of DHMBA and the like.

(Extraction)

Figure 2:
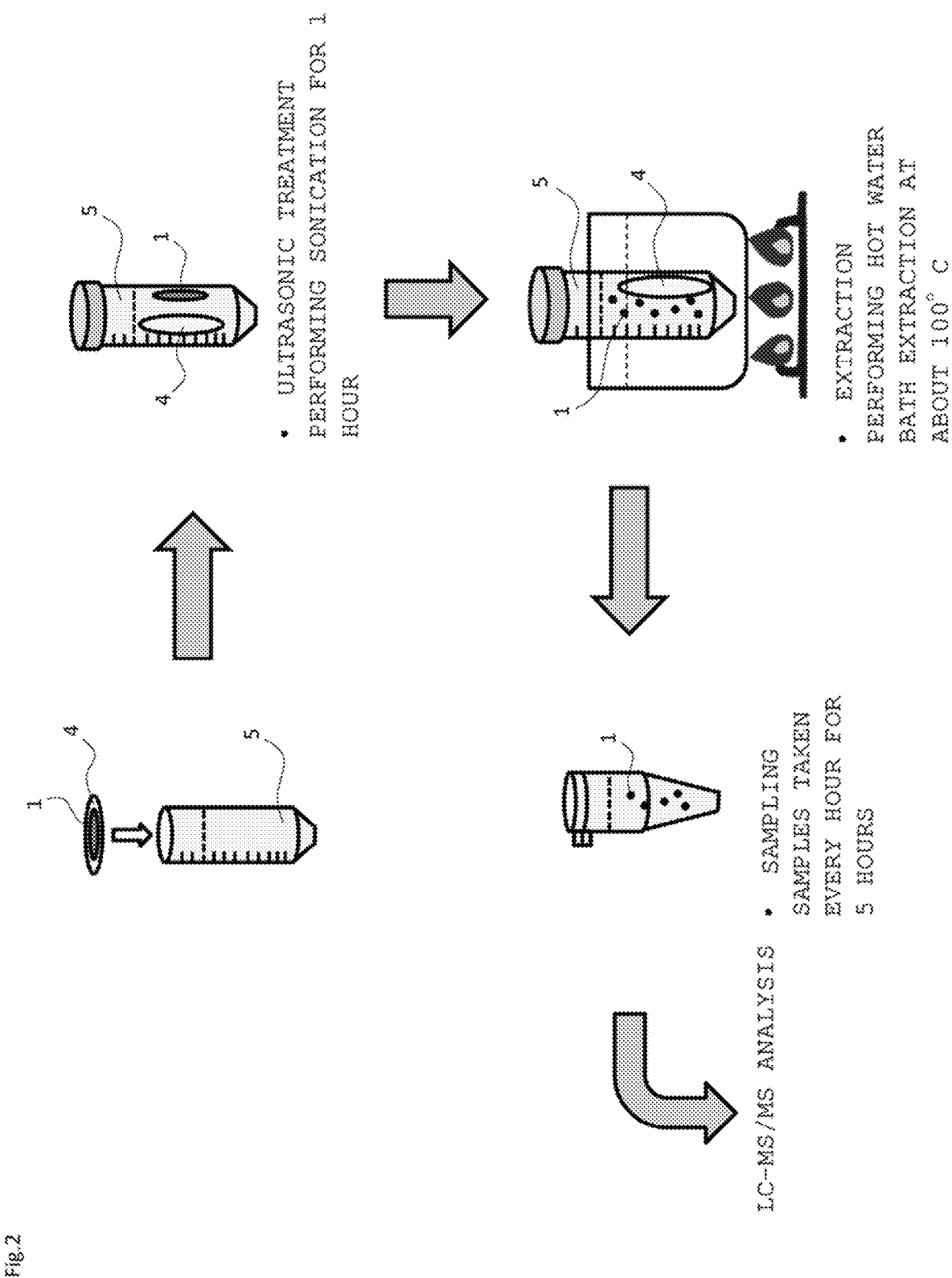
FIG. 2 is an explanatory diagram illustrating sonication of filtered plankton remained on a filter and subsequent heating extraction of DHMBA.

After the plankton 1 cells are destroyed by the aforementioned method such as sonication, the cells thus destroyed are heated to take out contents of the cells. That is, the aforementioned plankton and the like are subjected to hot water bath extraction at about 100° C. or the like (see FIG. 2).

In this operation, the plankton 1 in the aforementioned container 5 is heated in the hot water bath extraction and is not directly heated. That is, the container 5 is put into the hot water which is heated and stored in a beaker or the like to perform so-called indirect heating. This is advantageous, for example, in that stable heating extraction can be performed with a constant heating temperature.

(Sampling)

Then, samples were taken every hour for five hours during the aforementioned hot water bath extraction.

(Analysis of Useful Substance)

The concentration of DHMBA in the plankton 1 taken as the aforementioned sample was measured by LC-MS/MS.

(Result of Extraction Experiment with Samples in Hiroshima Sea Area)

As a result, DHMBA was not detected in the plankton before heating in both the aforementioned samples taken in the Hiroshima sea area in September 2016 and March 2017.

However, in the sample taken in the Hiroshima sea area in September, it could be confirmed that DHMBA was detected with an extraction amount of 0.303 (ng/L) after heating, that is, after the hot water bath extraction for 1 hour. Further, it could be confirmed that DHMBA was detected with an extraction amount of 0.297 (ng/L) after the hot water bath extraction for 2 hours and DHMBA was detected with an extraction amount of 0.279 (ng/L) after the hot water bath extraction for 3 hours. Further, it could be confirmed that DHMBA was detected with an extraction amount of 0.274 (ng/L) after the hot water bath extraction for 4 hours and DHMBA was detected with an extraction amount of 0.217 (ng/L) after the hot water bath extraction for 5 hours.

Figure 4:
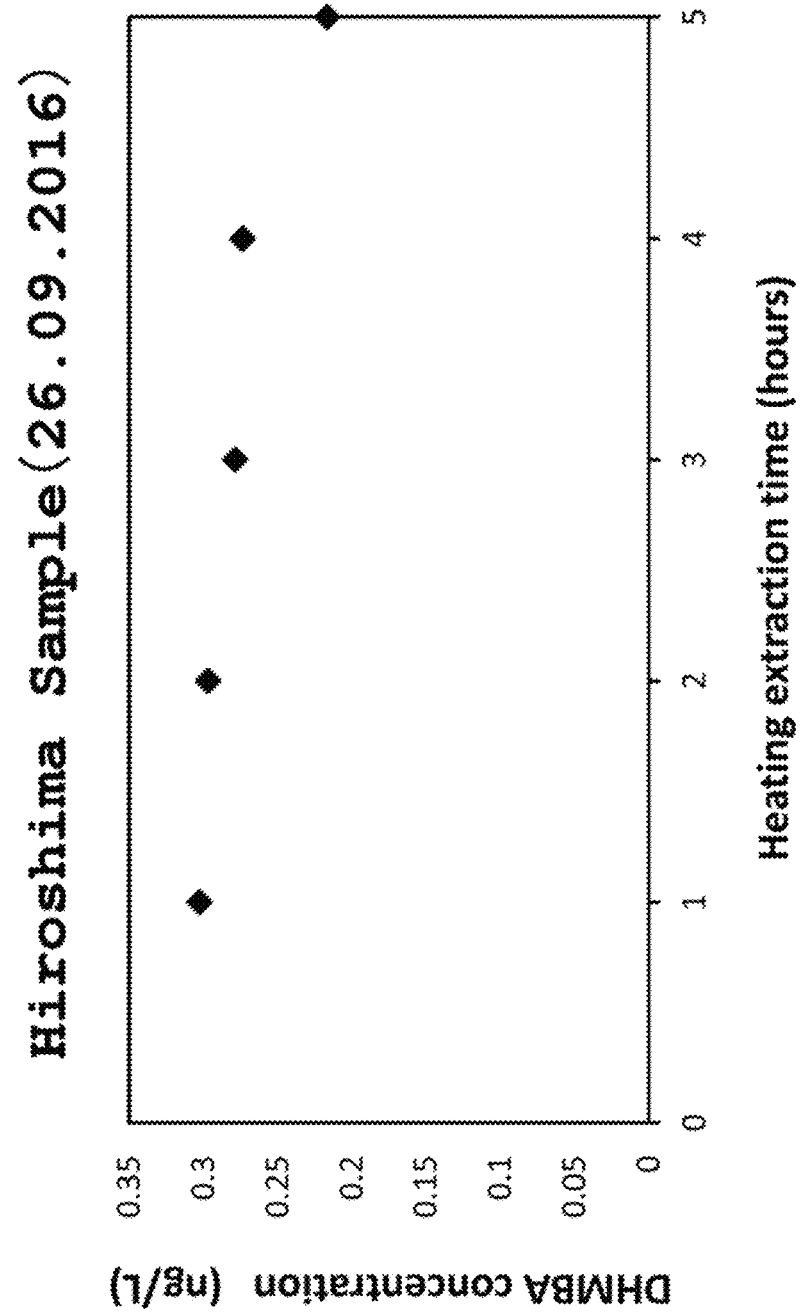
FIG. 4 is an explanatory diagram (1) illustrating whether or not DHMBA is produced when the plankton present in the seawater collected in a predetermined sea area in Hiroshima, Japan, at a predetermined period are heated.
Figure 5:
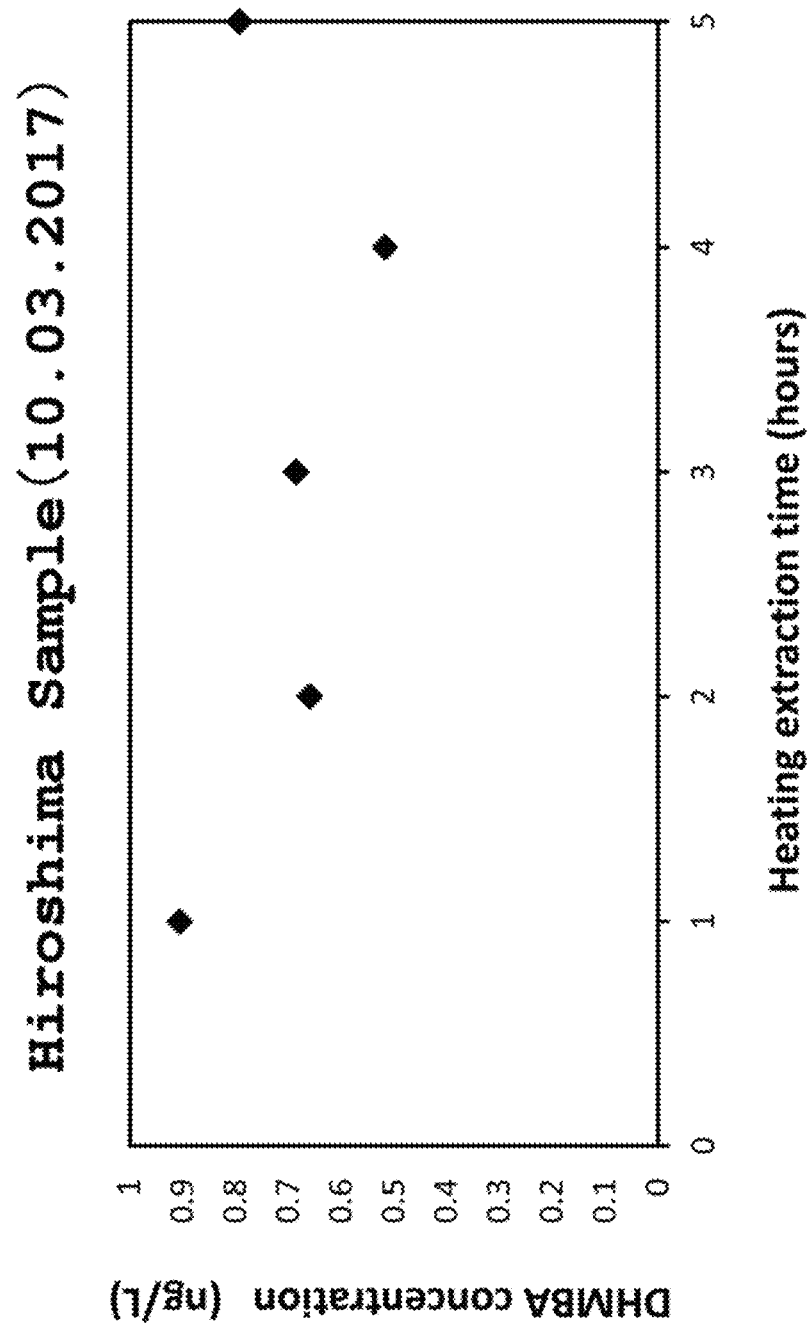
FIG. 5 is an explanatory diagram (2) illustrating whether or not DHMBA is produced when the plankton present in the seawater collected in the predetermined sea area in Hiroshima, Japan, at the predetermined period are heated.

Further, in the sample taken in the Hiroshima sea area in March, it could be confirmed that DHMBA was detected with an extraction amount of 0.906 (ng/L) after heating, that is, after the hot water bath extraction for 1 hour. Further, it could be confirmed that DHMBA was detected with an extraction amount of 0.66 (ng/L) after the hot water bath extraction for 2 hours and DHMBA was detected with an extraction amount of 0.686 (ng/L) after the hot water bath extraction for 3 hours. Further, it could be confirmed that DHMBA was detected with an extraction amount of 0.517 (ng/L) after the hot water bath extraction for 4 hours and DHMBA was detected with an extraction amount of 0.794 (ng/L) after the hot water bath extraction for 5 hours (see FIG. 4 and FIG. 5).

(Result of Extraction Experiment with Samples in Miyagi Sea Area)

Figure 6:
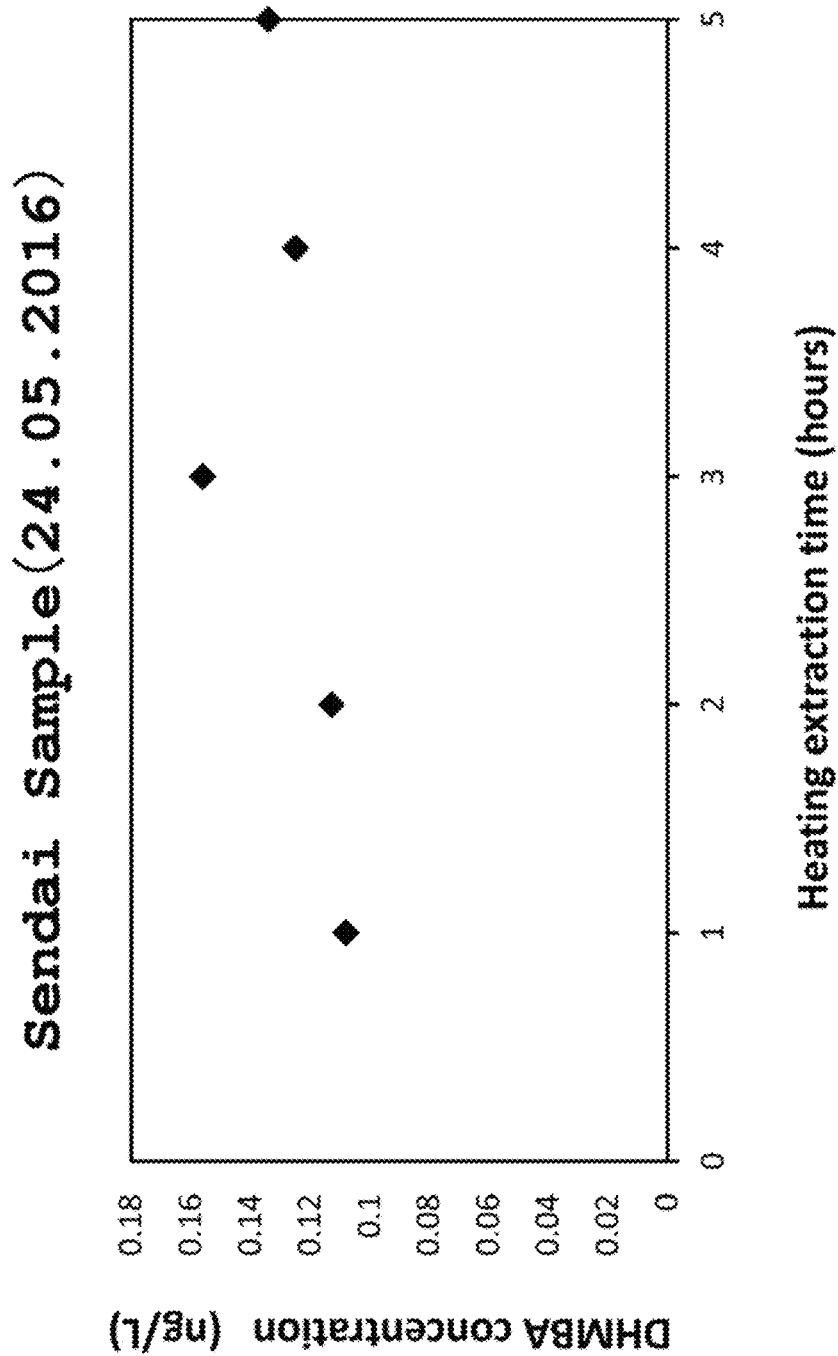
FIG. 6 is an explanatory diagram illustrating whether or not DHMBA is produced when the plankton present in the seawater collected in a predetermined sea area in Miyagi, Japan, at a predetermined period are heated.

FIG. 6 shows a detection result of DHMBA with samples taken in the Miyagi sea area in May 2016.

FIG. 6 shows changes in the extraction amount of DHMBA over time. Same as the sample in the Hiroshima sea area, DHMBA was not detected in the plankton before heating in the sample before heating. However, it could be confirmed that DHMBA was detected with an extraction amount of 0.108 (ng/L) after heating, that is, after the hot water bath extraction for 1 hour. Further, it could be confirmed that DHMBA was detected with an extraction amount of 0.113 (ng/L) after the hot water bath extraction for 2 hours and DHMBA was detected with an extraction amount of 0.156 (ng/L) after the hot water bath extraction for 3 hours. Further, it could be confirmed that DHMBA was detected with an extraction amount of 0.125 (ng/L) after the hot water bath extraction for 4 hours and DHMBA was detected with an extraction amount of 0.134 (ng/L) after the hot water bath extraction for 5 hours (see FIG. 6).

Note that the heating time is not limited to one-hour time lapse interval. DHMBA may be detected with a heating time of less than one hour.

In any case, it was found that DHMBA was not detected in the plankton which were not heated, while DHMBA could be quickly detected in the plankton which were heated.

Next, detection of DHMBA after pressurization will be described.

First, the seawater was collected in an actual sea area where oyster farming was performed (e.g., a sea area in Miyagi, Japan).

(Collection of Seawater Including Plankton)

The seawater is pumped up by a pump or the like in the sea area where oyster farming is performed (e.g., the sea area in Miyagi, Japan) at a predetermined period. Specifically, the seawater including the plankton is pumped up in the sea area in Miyagi in May 2016.

Note that, in the present example, the seawater in the sea areas in Miyagi was collected. However, the invention is not limited to the seawater in Miyagi. Further, regarding the period, the invention is not limited to the seawater in May.

(Filtration of Seawater Including Plankton)

The seawater including the plankton 1 was collected and then filtrated through a filter formed of a nonwoven fabric or the like, for example, a GF/C filter 4 (see FIG. 1).

In this operation, the amount of the seawater to be filtered was not limited. This time, about 3100 liters of seawater was collected in the sea area in Miyagi and filtered through the filter.

Note that the filter used for filtration in the above method has a large amount of the plankton 1 adhered thereon, and the filter on which the plankton 1 are adhered can be frozen and stored until an extraction operation is performed.

(Ultrasonic Treatment)

Next, for example, in a case where the filter on which the plankton 1 are adhered is frozen and stored, the filter which is frozen and stored is put into a container 5 such as a centrifuge tube, the container 5 is filled with, for example, ultrapure water, and the plankton 1 are further subjected to, for example, sonication using ultrasonic waves for about 1 hour or a ball mill treatment to destroy cell walls, thereby facilitating extraction of DHMBA and the like.

(Extraction)

Figure 3:
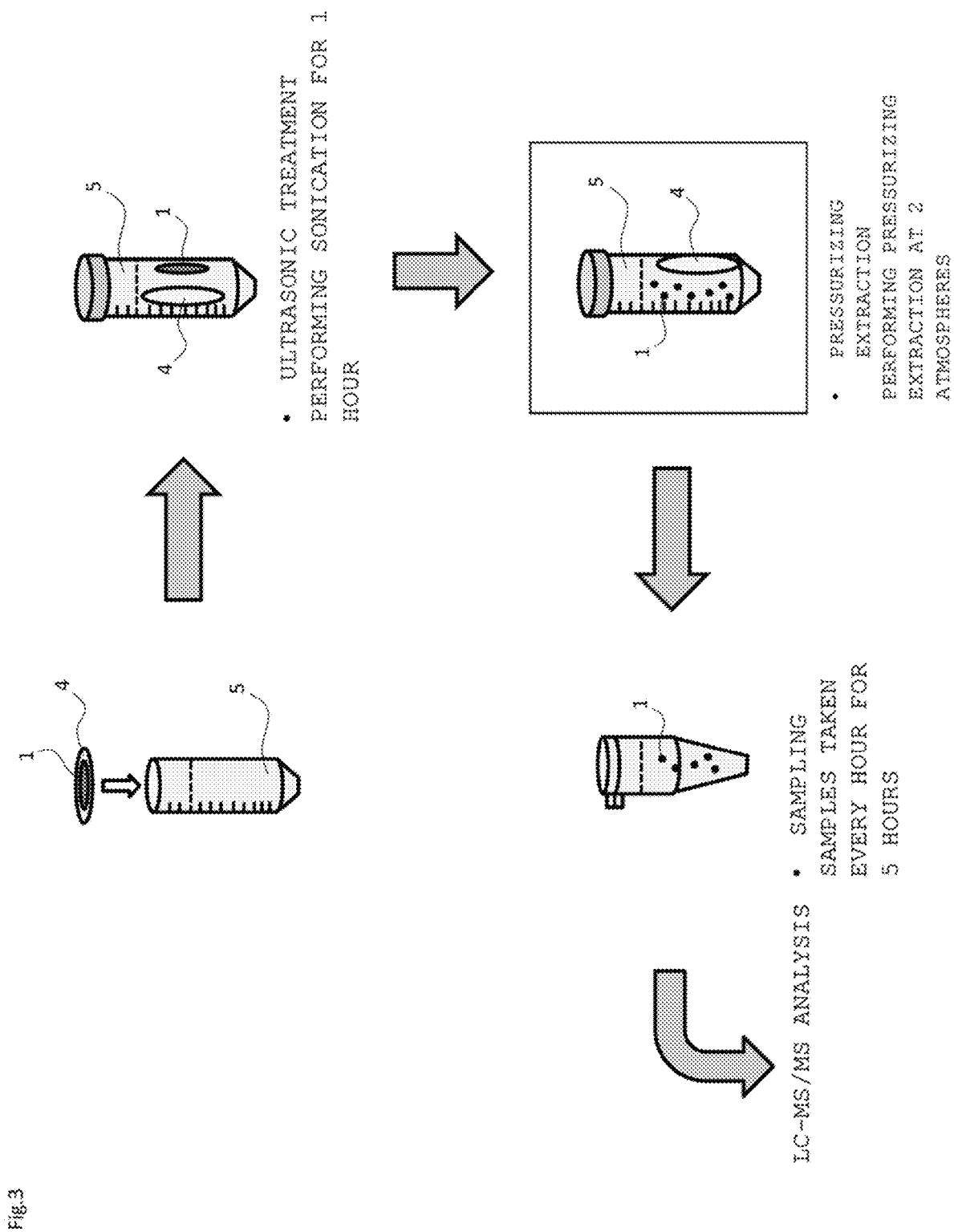
FIG. 3 is an explanatory diagram illustrating sonication of filtered plankton remained on a filter and subsequent pressurizing extraction of DHMBA.

Subsequently, after the plankton 1 cells are destroyed by the aforementioned method such as sonication, the cells thus destroyed are pressurized to take out contents of the cells. That is, the aforementioned plankton and the like were pressurized to about 2 atmospheres to perform extraction (see FIG. 3).

In this operation, the pressurizing method is not limited. As a general method, a pressure pot may be used for performing pressurization. Further, other methods may be used for performing pressurization.

(Sampling)

Then, samples were taken every hour for five hours during the aforementioned pressurizing extraction.

(Analysis of Useful Substance)

The concentration of DHMBA in the plankton 1 taken as the aforementioned sample was measured by LC-MS/MS.

(Result of Extraction Experiment with Samples in Miyagi Sea Area)

Figure 7:
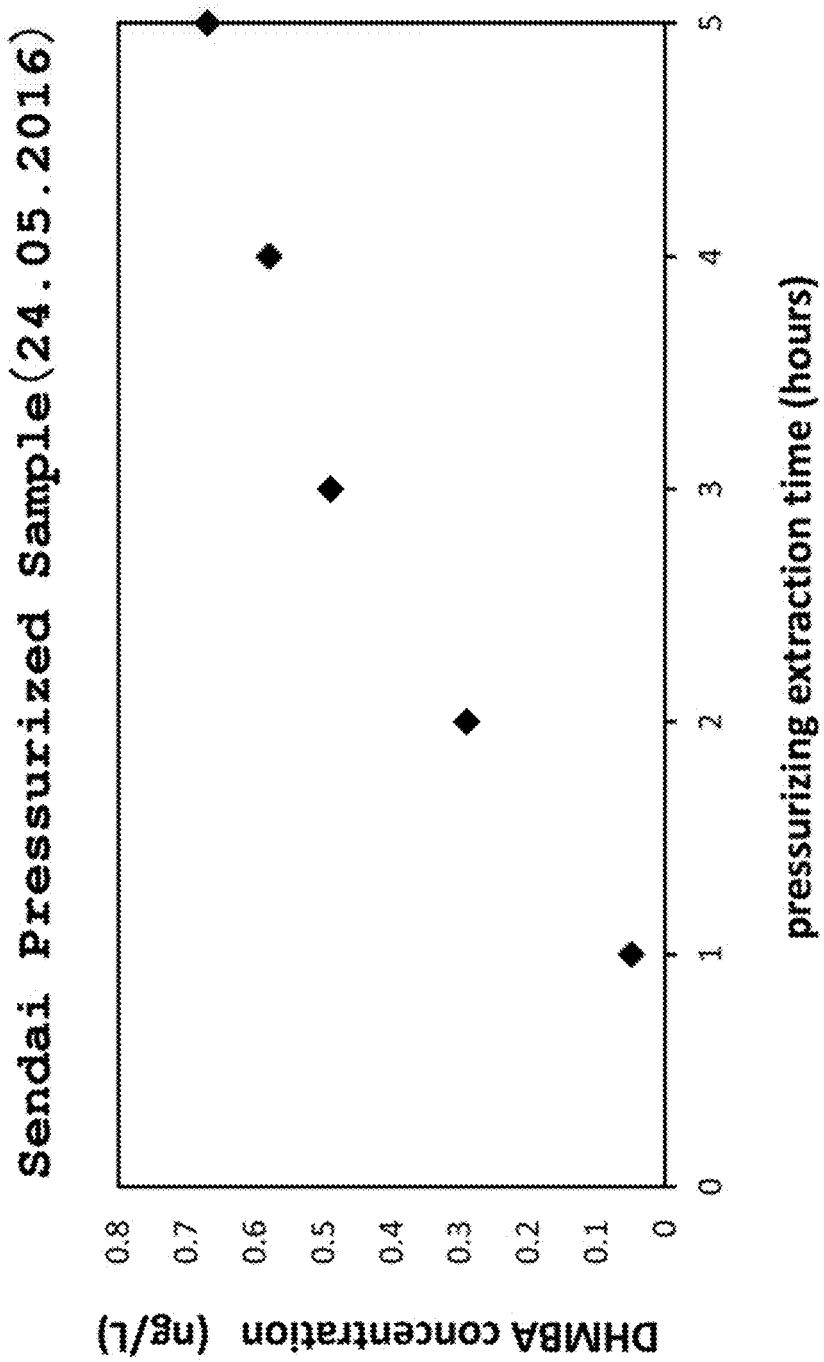
FIG. 7 is an explanatory diagram illustrating whether or not DHMBA is produced when the plankton present in the seawater collected in the predetermined sea area in Miyagi, Japan, at the predetermined period are pressurized.

FIG. 7 shows a detection result of DHMBA with samples taken in the Miyagi sea area.

FIG. 7 shows changes in the extraction amount of DHMBA over time. DHMBA was not detected in the plankton before pressurization. It could be confirmed that DHMBA was detected with an extraction amount of 0.05 (ng/L) after pressurization at 2 atmospheres, that is, after pressurization at 2 atmospheres for 1 hour. Further, it could be confirmed that DHMBA was detected with an extraction amount of 0.29 (ng/L) after pressurization at 2 atmospheres for 2 hours and DHMBA was detected with an extraction amount of 0.49 (ng/L) after pressurization at 2 atmospheres for 3 hours. Further, it could be confirmed that DHMBA was detected with an extraction amount of 0.58 (ng/L) after pressurization at 2 atmospheres for 4 hours and DHMBA was detected with an extraction amount of 0.67 (ng/L) after pressurization at 2 atmospheres for 5 hours (see FIG. 7).

In any case, it was found that DHMBA was not detected in the plankton which were not pressurized, while DHMBA could be quickly detected in the plankton which were pressurized.

(Identification of Plankton 1 in which DHMBA can be Detected)

There are many kinds of the plankton 1 in the seawater and it was unclear in which kinds of the plankton 1 DHMBA was detected. Thus, the present inventor decided to identify the plankton 1 in which DHMBA was detected.

The present inventor collected the seawater as described above to obtain the plankton 1 included in the seawater.

Among many kinds of the plankton 1 thus obtained, about 200 kinds of the plankton 1 were selected and cultured separately.

Then, about 200 kinds of the plankton thus cultured were subjected to the aforementioned DHMBA extraction treatment. That is, the plankton were subjected to the aforementioned ultrasonic treatment, the aforementioned extraction treatment with heating or pressurization, and the like.

As a result, DHMBA was detected in 4 microalgal strains in the plankton 1. Further, detailed morphological observation of these 4 microalgal strains could identify them as diatoms.

Note that diatoms are most ubiquitous in phytoplankton and diverse in many kinds.

However, when the present inventor observed the morphology of the aforementioned 4 microalgal strains in which DHMBA was detected in detail using a microscope, all 4 strains turned out to be diatoms. The microscope used in this observation has 1,000-fold magnification (ocular lens: 10-fold, objective lens: 100-fold).

The aforementioned 4 microalgal strains, that is, the diatoms, are members of marine diatoms widespread in the seawater in bays and known to abundantly produce unsaturated fatty acids. Further, they are also known as superplanktonic diatoms.

Next, the present inventor planned to per form DNA analysis of the aforementioned 4 microalgal strains, that is, the diatoms, for further specific identification of the diatoms.

The DNA analysis is performed to determine the taxonomic rank that the diatoms belong to. The aforementioned taxonomic rank is classified into "phylum", "subphylum", "class", "subclass", "order", "family", "genus", and "species", and the classification levels become more specific in the order from "phylum" to "species"

Processes of the DNA analysis will be described below.

Classification of Diatom (H-7-09 Strain) in which DHMBA is Detected

It is speculated that the diatom belongs to the subclass Bacillariophycidae. However, classification was not made at the level of "order" or below.

(Method)

Performing megaBLAST search with GenBank (NCBI, NHI)

Search condition (1) global search excluding environmental sequences (FIG. 8, FIG. 9)
→Discussion will be provided based on these results. Search condition (2) search limited to sequences from type material (FIG. 10, FIG. 11)
→Discussion will not be provided based on these results due to insufficient information amount of sequence data for comparison.

Figure 8:
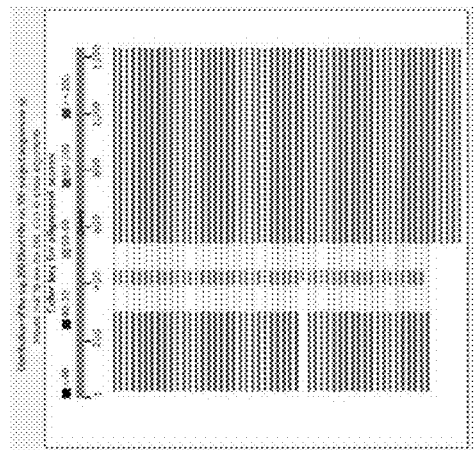
FIG. 8 is an explanatory diagram (1) illustrating a global search result under a search condition excluding environmental sequences.
Figure 9:
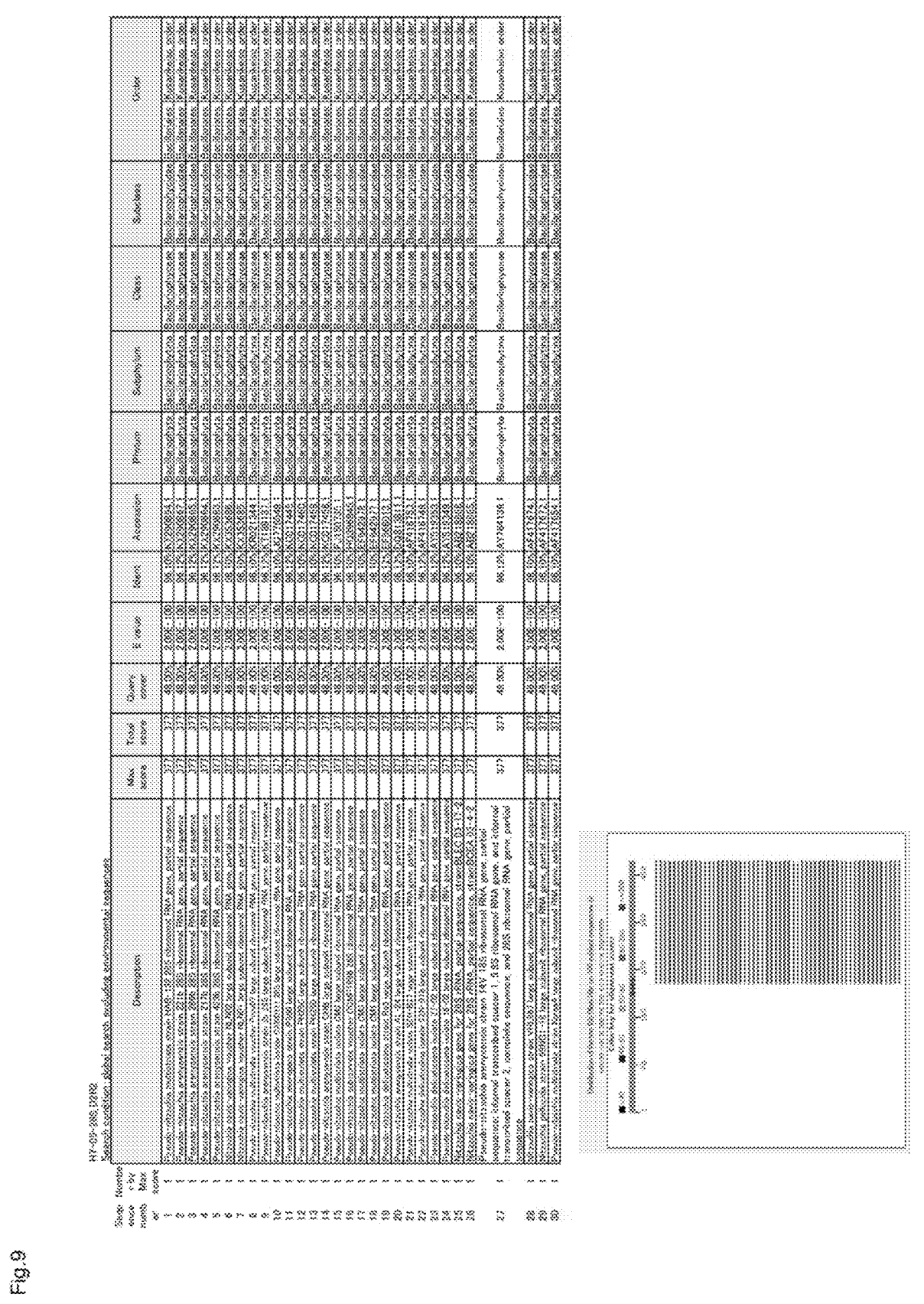

| Site | Sequence name | Base sequence length used for analysis | Sequence assembly | Blast analysis result |
|---|---|---|---|---|
| 18S | H7-09-18S | 1223 bp | Performed | FIG. 8 |
| 28S | H7-09-28S-D2R2 | 474 bp | Not performed | FIG. 9 |

(megaBLAST Search Result)

18S

Showing about 96.2% homology with the sequence of the Humidophila schmassmannii isolate HYU-D030 strain.
→Homology is as low as about 96%.

However, considering sequences found in the second and following places, it is speculated that the diatom belongs to the class Bacillariophyceae, the subclass Bacillariophycidae.

28S D2R2 Sequence

Showing about 96.1% homology with the sequence of the Pseudo-nitzschia multistriata HAB-132 strain.
→Homology is as low as about 96%. Further, short sequence and low score and coverage make the classification result less reliable as compared with the result of 18S.

However, the result is not contradictory to the possibility that the diatom belongs to the subclass Bacillariophycidae as speculated from the result of 18S.

(Classification Result)

It is speculated that the diatom belongs to the phylum Bacillariophyta, the subphylum Bacillariophytina, the class Bacillariophyceae, the subclass Bacillariophycidae.

However, classification cannot be made at the level of "order" or below.

Classification of diatom (H-9-05 strain) in which DHMBA is detected

It is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

However, classification was not made at the level of "species".

(Method)

Performing megaBLAST search with GenBank (NCBI, NHI)

Search condition (1) global search excluding the environmental sequences (FIG. 12, FIG. 13, FIG. 14)
→Discussion will be provided based on these results.

Figure 15:
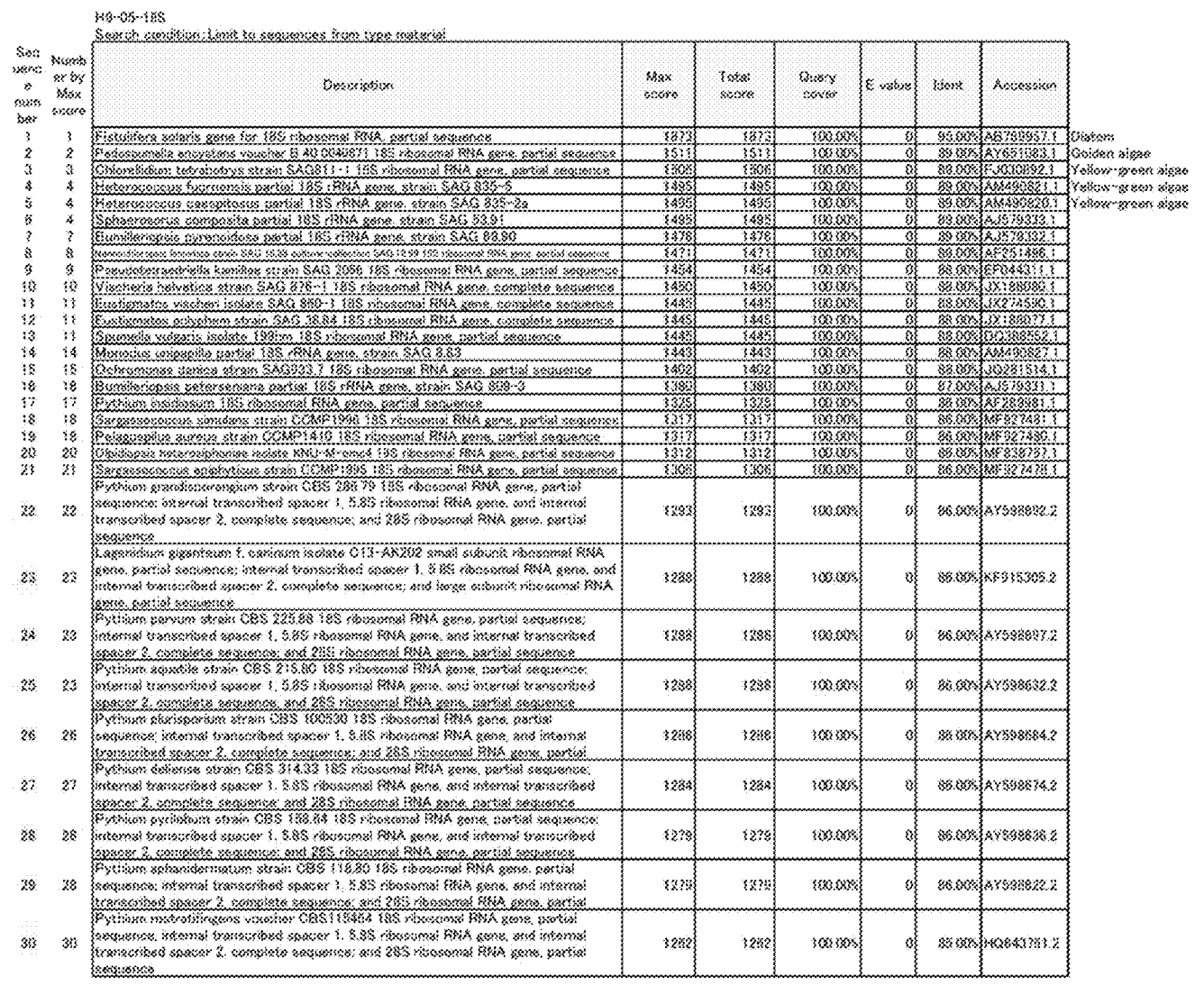

Search condition (2) search limited to the sequences from type material (FIG. 15, FIG. 16, FIG. 17)

→Discussion will not be provided based on these results due to insufficient information amount of sequence data for comparison.

Figure 12:
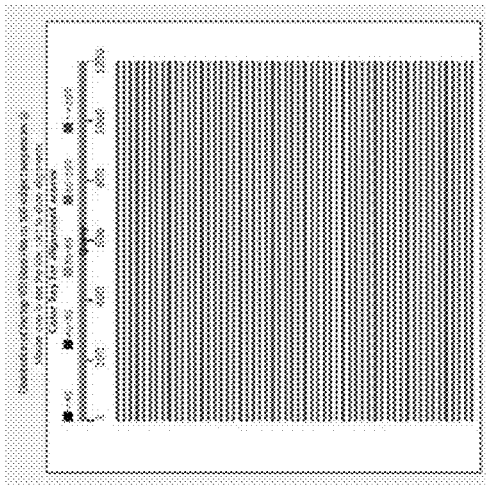
FIG. 12 is an explanatory diagram (3) illustrating the global search result under the search condition excluding the environmental sequences.
Figure 13:
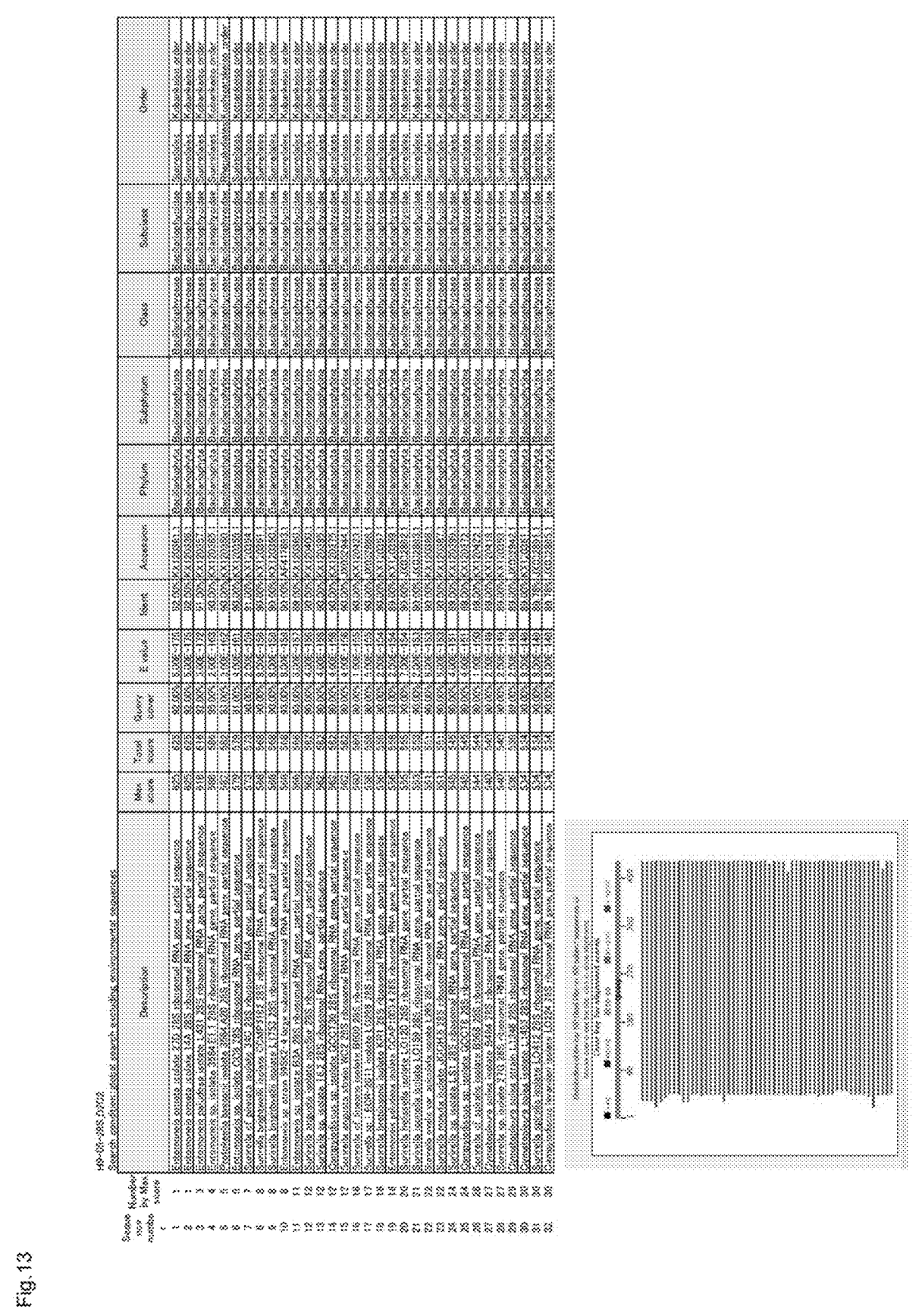
Figure 14:
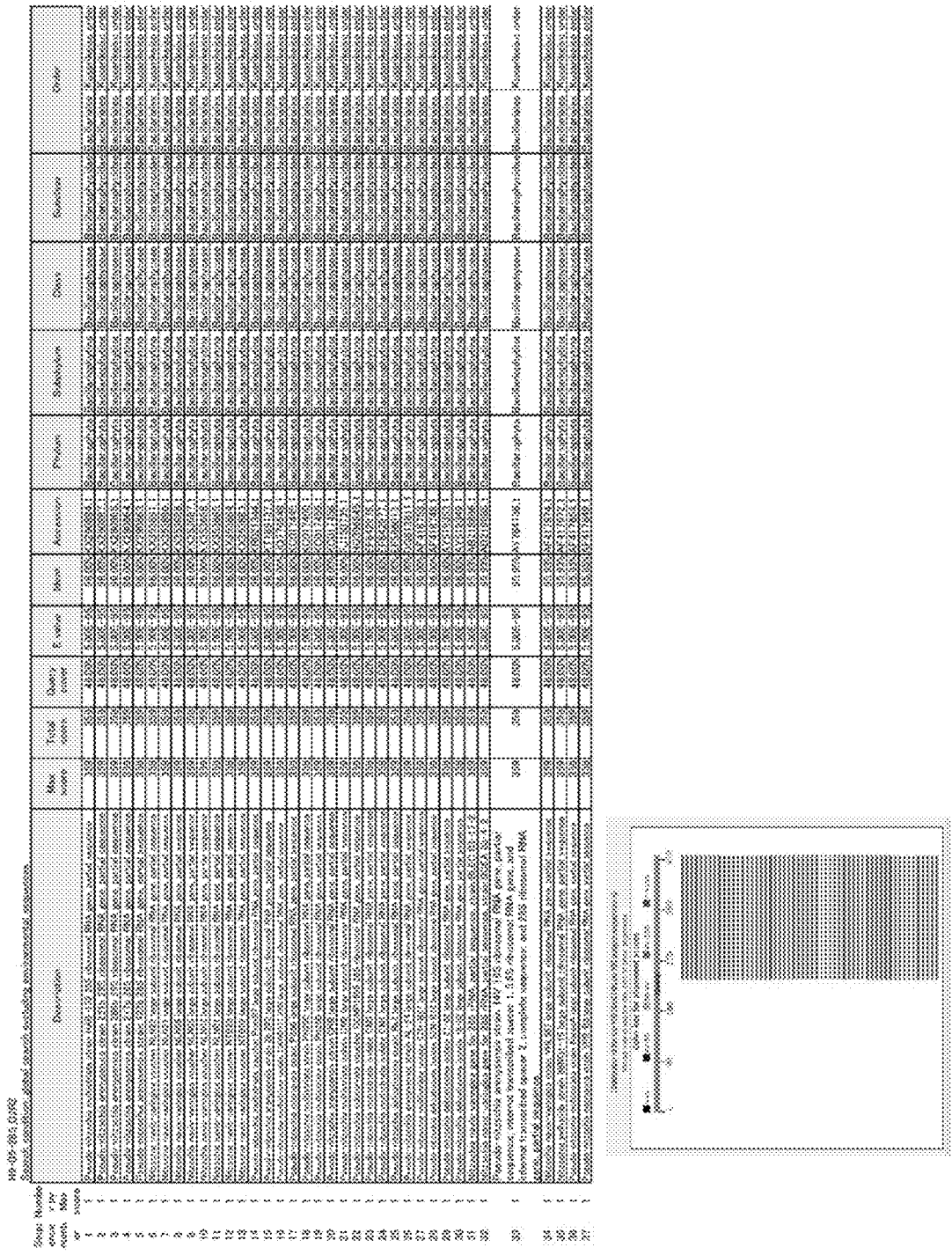
FIG. 14 is an explanatory diagram (5) illustrating the global search result under the search condition excluding the environmental sequences.

| Site | Sequence name | Base sequence length used for analysis | Sequence assembly | Blast analysis result |
|---|---|---|---|---|
| 18S | H9-05-18S | 1204 bp | Performed | FIG. 12 |
| 28S | H9-05-28S-D2C2 | 480 bp | Not performed | FIG. 13 |
| 28S | H9-05-28S-D2R2 | 458 bp | Not performed | FIG. 14 |

(megaBLAST Search Result)

18S

Showing 98% homology with the sequence of the Entomoneis paludosa L431 strain.

→Homology is as low as 98%. However, considering that sequences of the genus Entomoneis are found in the second and following places, it is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

28S D2C2 sequence

Showing about 92% homology with the sequence of the Entomoneis ornata 27D strain.

→It has a very low homology of 92%, providing less useful information. Further, short sequence and low score and coverage make the classification result significantly less reliable as compared with the result of 18S.

However, the result is not contradictory to the possibility that the diatom belongs to the genus Entomoneis as speculated from the result of 18S.

28S D2R2 sequence

Showing about 96% homology with the sequence of the Pseudo-nitzschia multistriata HAB-132 strain.

→It has a low homology of 96%, providing less useful information. Further, short sequence and low score and coverage as compared with D2C2 make the classification result significantly less reliable.

However, the result is not contradictory to the possibility that the diatom belongs to the subphylum Bacillariophytina as speculated from the result of 18S.

(Classification Result)

It is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

However, classification was not made at the level of "species".

Classification of diatom (H-9-06 strain) in which DHMBA is detected

It is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

However, classification was not made at the level of "species".

(Method) Performing megaBLAST search with GenBank (NCBI, NHI)

Figure 18:
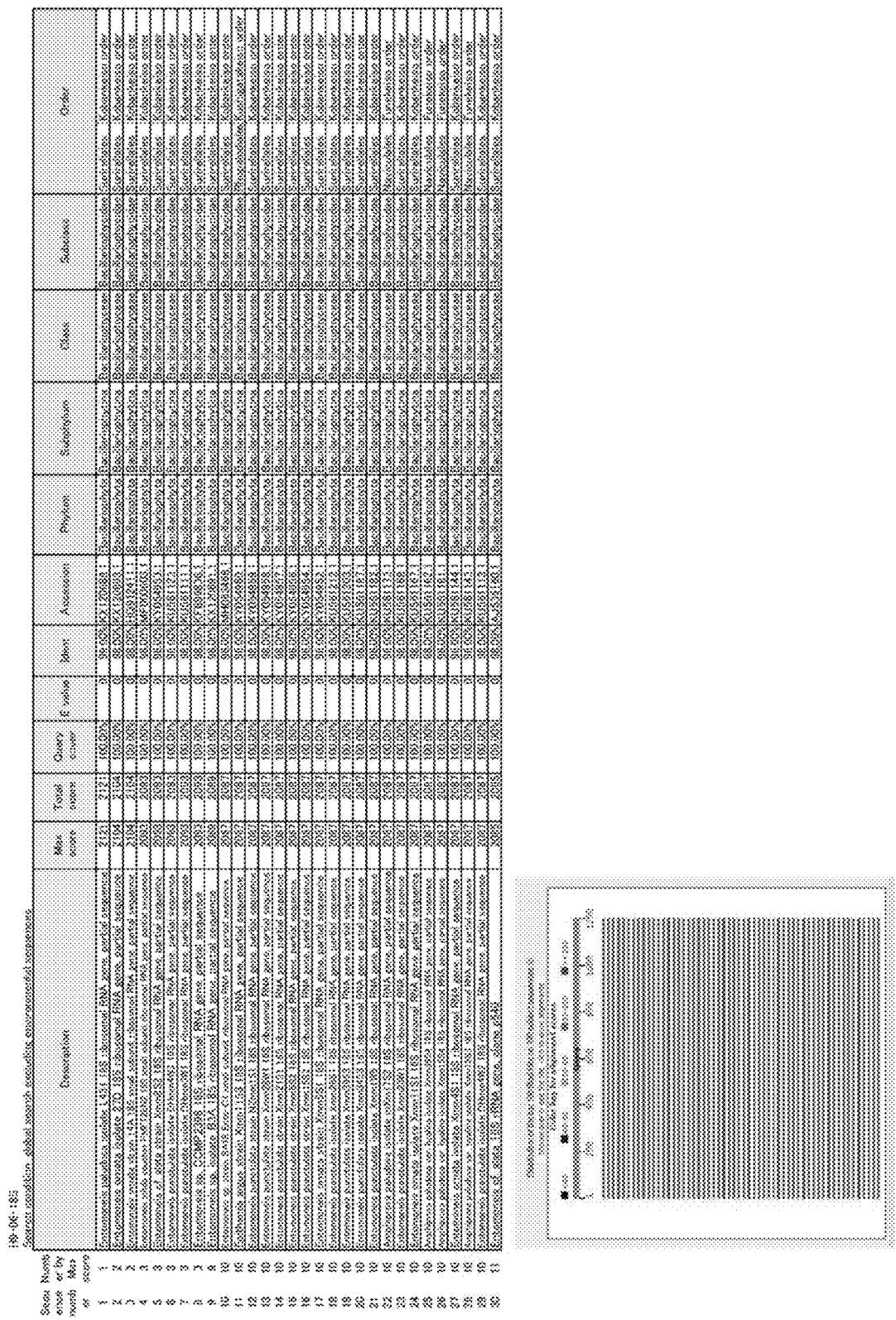
FIG. 18 is an explanatory diagram (6) illustrating the global search result under the search condition excluding the environmental sequences.
Figure 19:
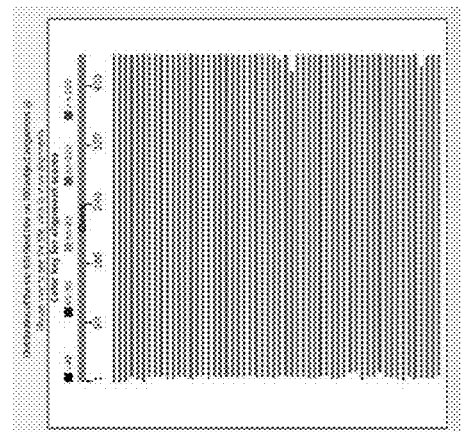
FIG. 19 is an explanatory diagram (7) illustrating the global search result under the search condition excluding the environmental sequences.
Figure 20:
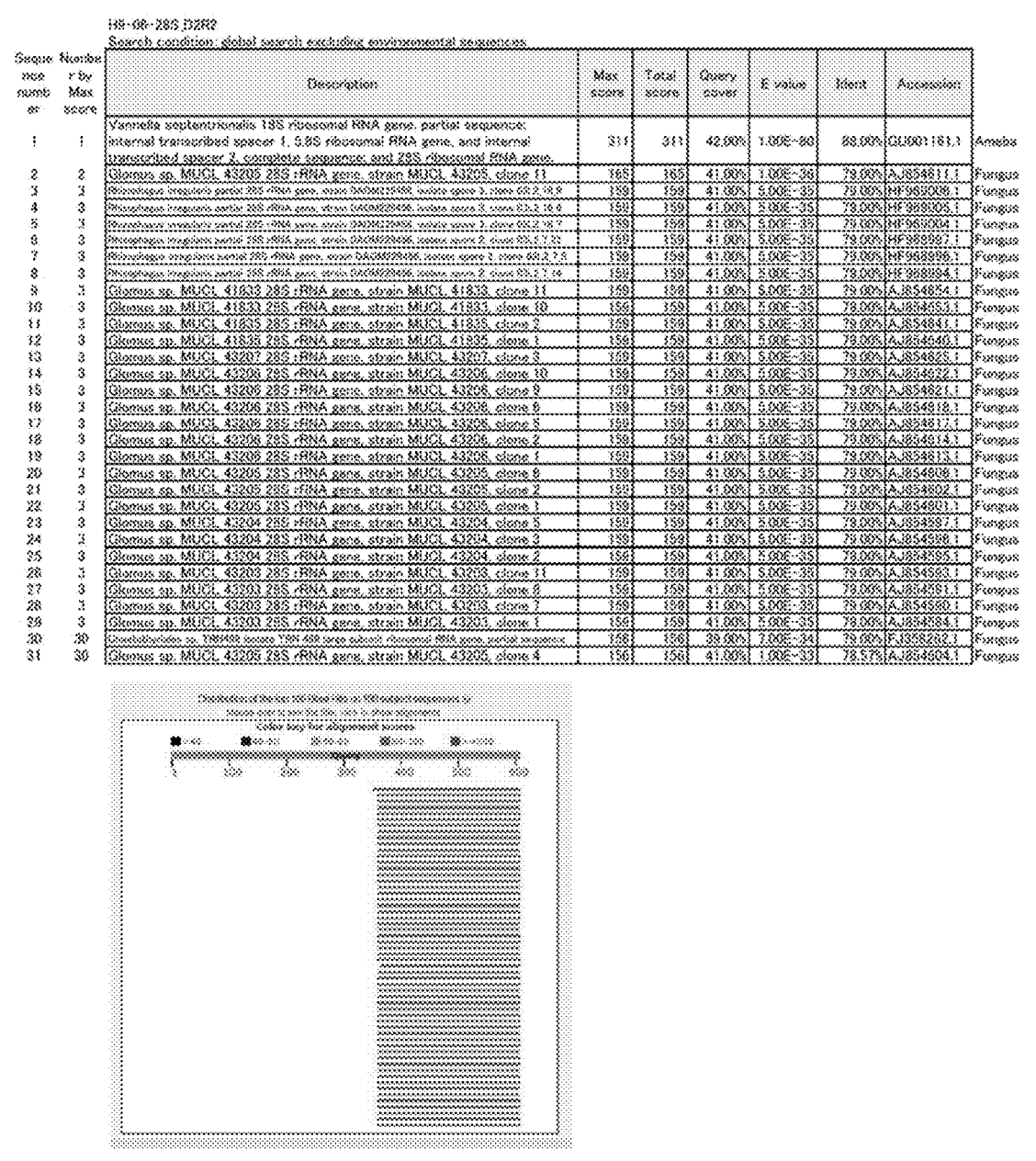

Search condition (1) global search excluding the environmental sequences (FIG. 18, FIG. 19, FIG. 20)

→Discussion will be provided based on these results.

Figure 21:
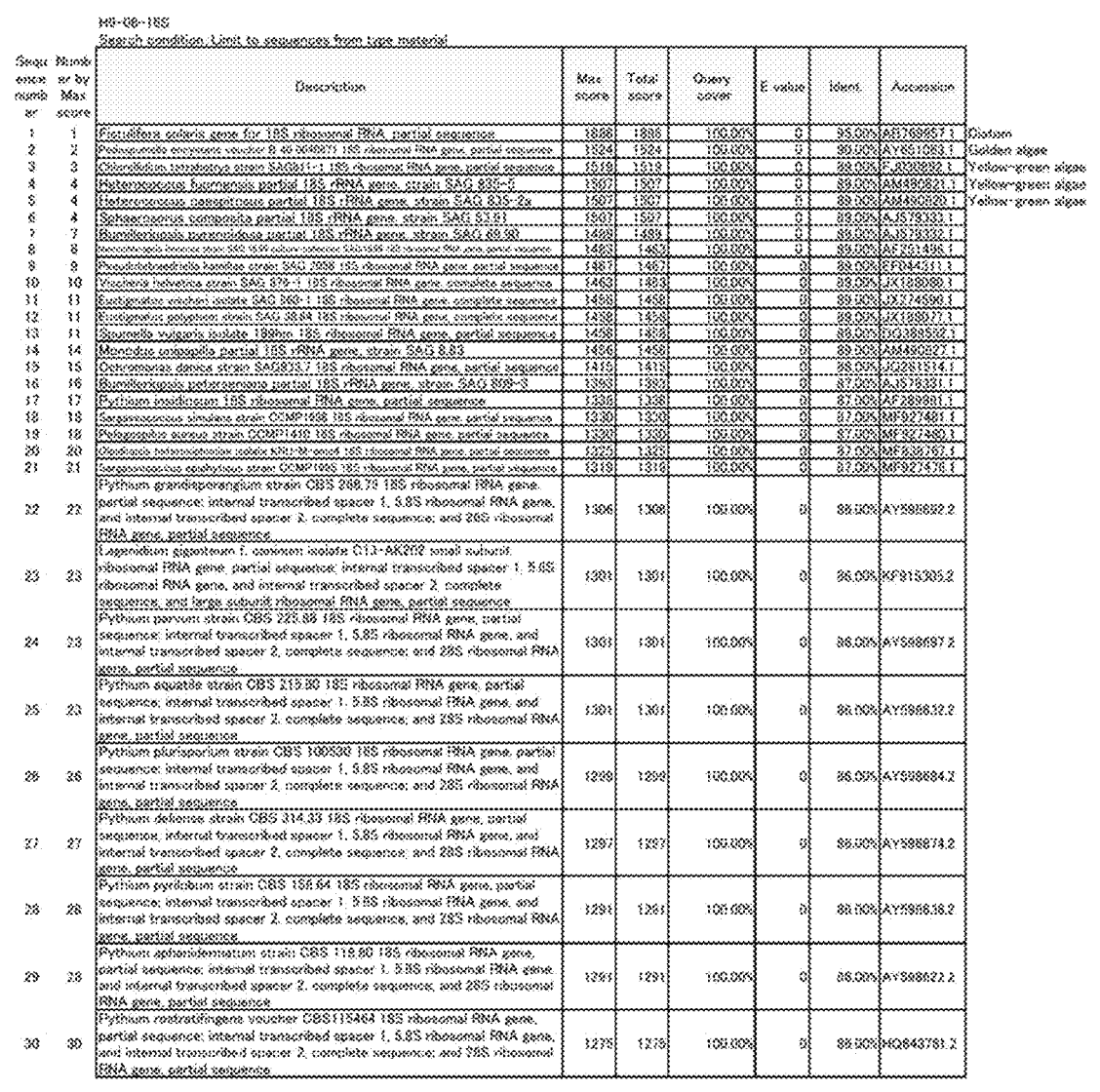
Figure 23:
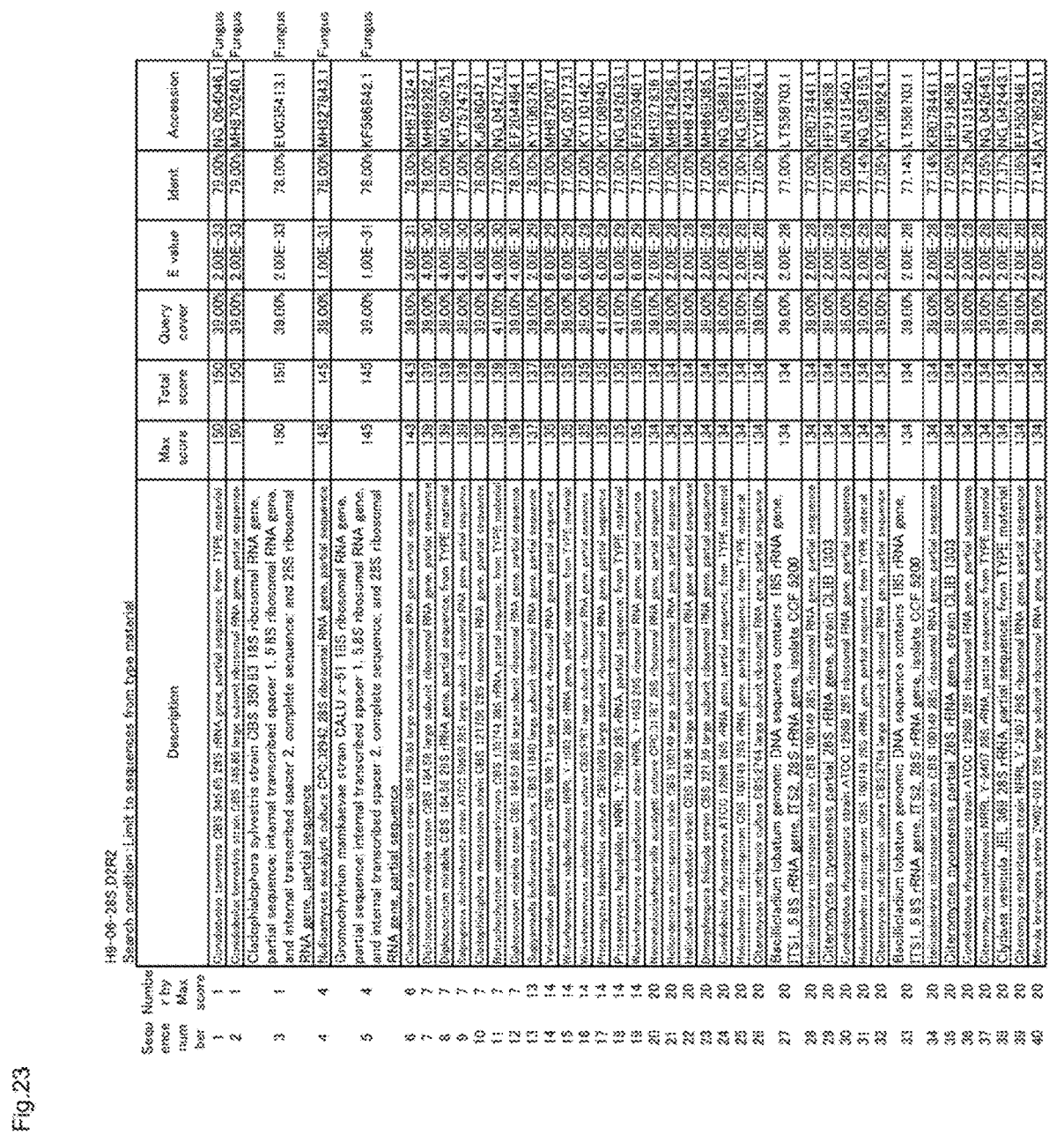

Search condition (2) search limited to the sequences from type material (FIG. 21, FIG. 22, FIG. 23)

→Discussion will not be provided based on these results due to insufficient information amount of sequence data for comparison.

| Site | Sequence name | Base sequence length used for analysis | Sequence assembly | Blast analysis result |
|---|---|---|---|---|
| 18S | H9-06-18S | 1204 bp | Performed | FIG. 18 |
| 28S | H9-06-28S-D2C2 | 440 bp | Not performed | FIG. 19 |
| 28S | H9-06-28S-D2R2 | 609 bp | Not performed | FIG. 20 |

(megaBLAST Search Result)

18S

Showing 99% homology with the sequence of the Entomoneis paludosa L431 strain.

→Considering that homology is 99% and sequences of the genus Entomoneis are found in the second and following places, it is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

28S D2C2 sequence

Showing 91% homology with the sequence of the Entomoneis ornata 27D strain.

→It has a very low homology of 91%, providing less useful information. Further, short sequence and low score make the classification result significantly less reliable as compared with the result of 18S.

However, the result is not contradictory to the possibility that the diatom belongs to the genus Entomoneis as speculated from the result of 18S.

28S D2R2 sequence

Showing 88% homology with Vannella septentrionalis (ameba).

Further, it had 79% or less homology with a fungus forming an arbuscular mycorrhiza.

→Homology is less than 90%. Further, short sequence and lower score and coverage as compared with D2C2 make the classification result significantly less reliable.

Thus, the result is excluded from the present discussion on classification.

(Classification Result)

It is speculated that the diatom belongs to the phylum Bacillariophyta, the subphylum Bacillariophytina, the class Bacillariophyceae, the subclass Bacillariophycidae, the order Surirellales, the family Entomoneidaceae, the genus Entomoneis.

H-9-09 strain Classification

Undetermined (Method) Performing megaBLAST Search with GenBank (NCBI, NHI)

Figure 24:
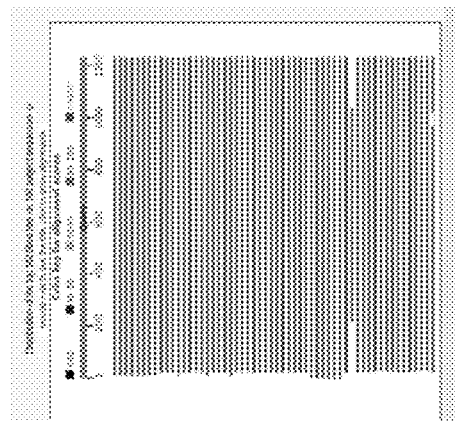
FIG. 24 is an explanatory diagram (9) illustrating the global search result under the search condition excluding the environmental sequences.
Figure 25:
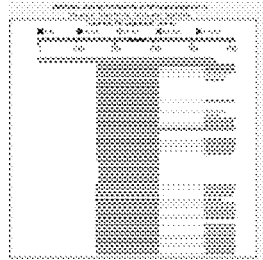
FIG. 25 is an explanatory diagram (10) illustrating the global search result under the search condition excluding the environmental sequences.
Figure 26:
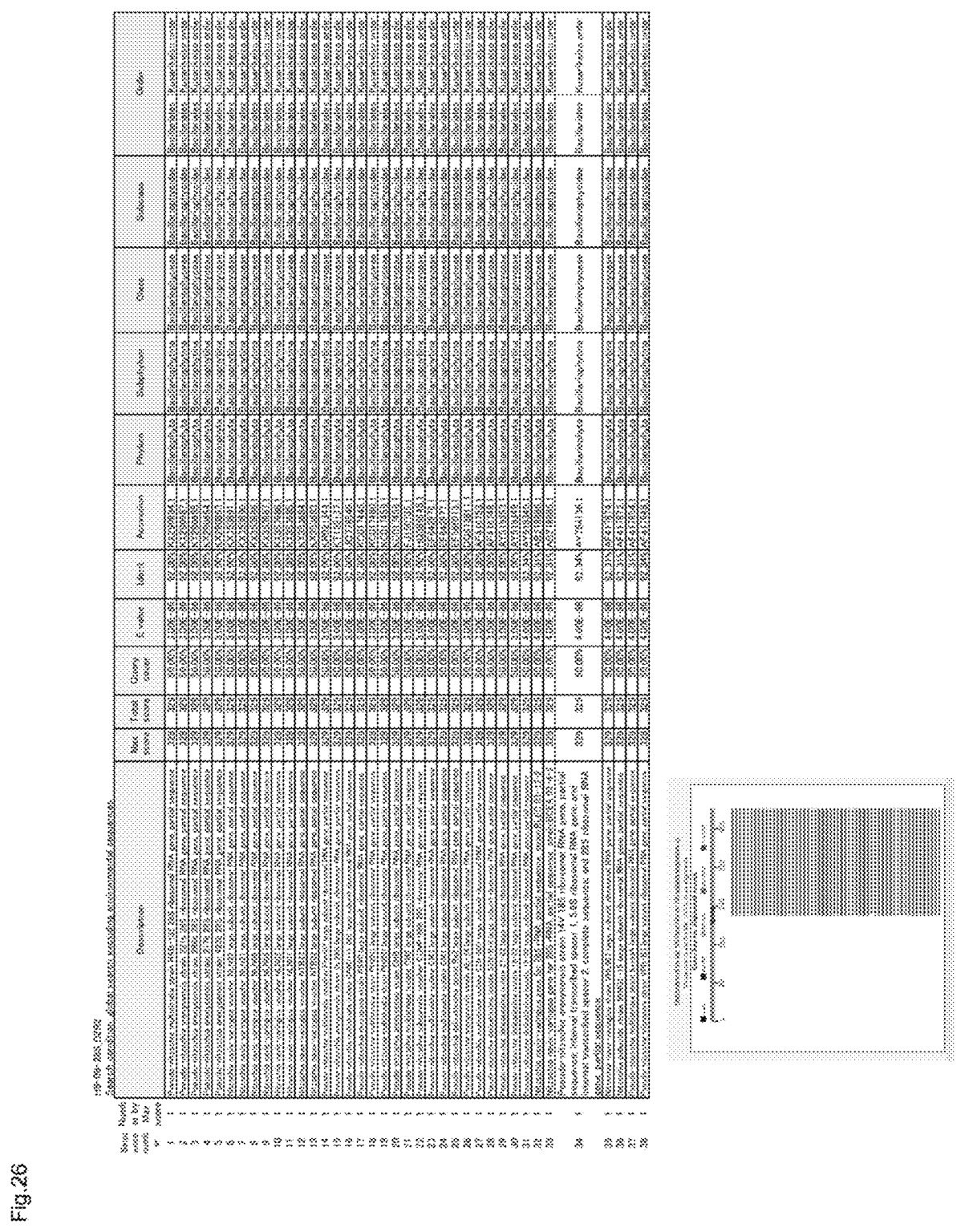

Search condition (1) global search excluding the environmental sequences (FIG. 24, FIG. 25, FIG. 26)

→Discussion will be provided based on these results.

Figure 28:
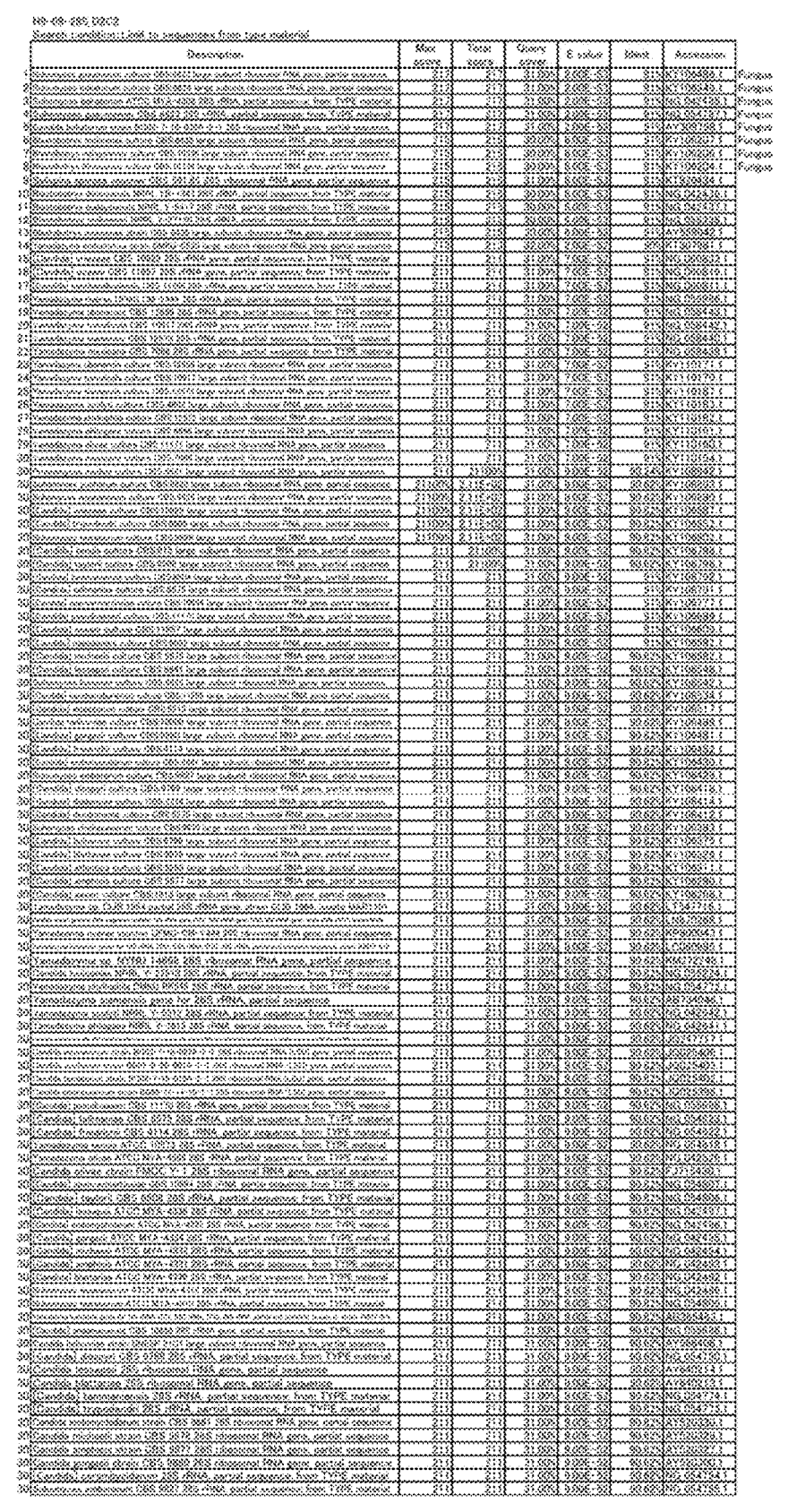

Search condition (2) search limited to the sequences from type material (FIG. 27, FIG. 28, FIG. 29)

→Discussion will not be provided based on these results due to insufficient information amount of sequence data for comparison.

| Site | Sequence name | Base sequence length used for analysis | Sequence assembly | Blast analysis result |
|---|---|---|---|---|
| 18S | H9-09-18S | 1228 bp | Performed | FIG. 24 |
| 28S | H9-09-28S-D2C2 | 511 bp | Not performed | FIG. 25 |
| 28S | H9-09-28S-D2R2 | 441 bp | Not performed | FIG. 26 |

(megaBLAST Search Result)

18S

Showing 97% homology with the sequence of the Caecitellus paraparvulus HFCC320 strain (Bicosoeca).

Sequences of diatoms of the same genus are found in the second and following places with a homology of 97%.

→It has a low homology of 97%. However, this cannot rule out the possibility that the sequence of a Bicosoeca is amplified.

However, prior microscopic observation confirmed that the specimen had a diatom-like morphology.

28S D2C2 sequence

Showing 88% homology with the sequence of the Caecitellus paraparvulus HFCC71 strain (Bicosoeca).

→Homology is less than 90%. Further, short sequence and lower score and coverage make the classification result significantly less reliable as compared with the result of 18S.

Thus, the result is excluded from the present discussion on classification.

However, the result is not contradictory to the result of 18S (indicating a Bicosoeca).

28S D2R2 sequence

Showing about 92% homology with the sequence of the Pseudo-nitzschia multistriata HAB-132 strain (subphylum Bacillariophytina).

→It has a low homology of 92%. Further, short sequence and low score and coverage make the classification result less reliable as compared with the result of 18S.

However, the result is not contradictory to the prior morphological observation (indicating a diatom).

(Classification Result)

Undetermined

REFERENCE SIGNS LIST

1 Plankton
4 GF/C filter
5 Container

The invention claimed is:

1. A method for producing 3,5-dihydroxy-4-methoxybenzyl alcohol from plankton, comprising:
 filtering collected seawater containing the plankton using a filter;
 taking out a cell content from the plankton remained on the filter; and then
 heating the cell content thus taken out to produce 3,5-dihydroxy-4-methoxybenzyl alcohol from a heated material thus heated, wherein
 the plankton is a diatom.

2. A method for producing 3,5-dihydroxy-4-methoxybenzyl alcohol from plankton, comprising:
 filtering collected seawater containing the plankton using a filter;
 taking out a cell content from the plankton remained on the filter; and then
 heating the cell content thus taken out to produce 3,5-dihydroxy-4-methoxybenzyl alcohol from a heated material thus heated, wherein
 the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

3. A method for producing 3,5-dihydroxy-4-methoxybenzyl alcohol from plankton, comprising:
 filtering collected seawater containing the plankton using a filter;
 crushing the plankton remained on the filter with an addition of an extracting solution, and
 extracting a cell content from the plankton followed by heating to produce 3,5-dihydroxy-4-methoxybenzyl alcohol from a heated material thus heated, wherein
 the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

4. The method for producing 3,5-dihydroxy-4-methoxybenzyl alcohol from the plankton according to claim 1, wherein the heating time is at least 1 hour or longer.

5. A method for producing 3,5-dihydroxy-4-methoxybenzyl alcohol from plankton, comprising:
 filtering collected seawater containing the plankton using a filter;
 taking out a cell content from the plankton remained on the filter, and then
 pressurizing the cell content thus taken out to produce 3,5-dihydroxy-4-methoxybenzyl alcohol from a pressurized material thus pressurized, wherein
 the plankton is a diatom.

6. A method for producing 3,5-dihydroxy-4-methoxybenzyl alcohol from plankton, comprising:
 filtering collected seawater containing the plankton using a filter;
 taking out a cell content from the plankton remained on the filter, and then
 pressurizing the cell content thus taken out to produce 3,5-dihydroxy-4-methoxybenzyl alcohol from a pressurized material thus pressurized, wherein
 the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

7. A method for producing 3,5-dihydroxy-4-methoxybenzyl alcohol from plankton, comprising:
 filtering collected seawater containing the plankton using a filter;
 crushing the plankton remained on the filter with an addition of an extracting solution, and
 extracting a cell content from the plankton followed by pressurization to produce 3,5-dihydroxy-4-methoxybenzyl alcohol from a pressurized material thus pressurized, wherein
 the plankton is a diatom belonging to the phylum Bacillariophyta, the subphylum Bacillariophytina, the class Bacillariophyceae, the subclass Bacillariophycidae or a diatom belonging to the phylum Bacillariophyta, the subphylum Bacillariophytina, the class Bacillariophyceae, the subclass Bacillariophycidae, the order Surirellales, the family Entomoneidaceae, the genus Entomoneis.

8. The method for producing 3,5-dihydroxy-4-methoxybenzyl alcohol from the plankton according to claim 5, wherein the pressurization is performed at at least 2 atmospheres or more.

9. The method for producing 3,5-dihydroxy-4-methoxybenzyl alcohol from the plankton according to claim 5, wherein the pressurizing time is at least 1 hour or longer.

10. The method for producing 3,5-dihydroxy-4-methoxybenzyl alcohol from the plankton according to claim 2, wherein the heating time is at least 1 hour or longer.

11. The method for producing 3,5-dihydroxy-4-methoxybenzyl alcohol from the plankton according to claim 6, wherein the pressurization is performed at at least 2 atmospheres or more.

12. The method for producing 3,5-dihydroxy-4-methoxybenzyl alcohol from the plankton according to claim 7, wherein the pressurization is performed at at least 2 atmospheres or more.

13. The method for producing 3,5-dihydroxy-4-methoxybenzyl alcohol from the plankton according to claim 6, wherein the pressurizing time is at least 1 hour or longer.

14. The method for producing 3,5-dihydroxy-4-methoxybenzyl alcohol from the plankton according to claim 7, wherein the pressurizing time is at least 1 hour or longer.

* * * * *